(12) United States Patent  
Maier et al.

(10) Patent No.: US 8,575,193 B2  
(45) Date of Patent: Nov. 5, 2013

(54) N-SUBSTITUTED TETRAHYDROISOQUINOLINE/ISOINDOLINE HYDROXAMIC ACID COMPOUNDS

(75) Inventors: Thomas Maier, Stockach (DE); Thomas Beckers, Freiburg (DE); Barbara Beckers, legal representative, Freiburg (DE); Christian Hesslinger, Zoznegg (DE)

(73) Assignee: 4SC AG, Martinsried (DE)

( * ) Notice: Subject to any disclaimer, the term of this patent is extended or adjusted under 35 U.S.C. 154(b) by 6 days.

(21) Appl. No.: 12/921,821

(22) PCT Filed: Mar. 12, 2009

(86) PCT No.: PCT/EP2009/052924  
§ 371 (c)(1),  
(2), (4) Date: Apr. 29, 2011

(87) PCT Pub. No.: WO2009/112550  
PCT Pub. Date: Sep. 17, 2009

(65) Prior Publication Data  
US 2011/0201643 A1   Aug. 18, 2011

(30) Foreign Application Priority Data  
Mar. 13, 2008 (EP) .................................... 08004661

(51) Int. Cl.  
*C07D 217/06* (2006.01)  
*C07D 401/02* (2006.01)  
*A61K 31/472* (2006.01)

(52) U.S. Cl.  
USPC ........... 514/307; 514/314; 514/339; 514/416; 546/146; 546/169; 548/469

(58) Field of Classification Search  
None  
See application file for complete search history.

(56) References Cited

FOREIGN PATENT DOCUMENTS

WO    2005/108367 A1    11/2005

OTHER PUBLICATIONS

West, Anthony R., Solid State Chemistry and its Applications, Wiley, New York, 1988, pp. 358 & 365.*

* cited by examiner

*Primary Examiner* — Zinna Northington Davis  
(74) *Attorney, Agent, or Firm* — Millen, White, Zelano & Branigan, P.C.

(57) ABSTRACT

Compounds of a certain formula (I) wherein R1, R2, R3, X, Y, r, s, t, u and v have the meanings as defined in the specification, and the salts, solvates and hydrates thereof are novel effective HDAC 6 inhibitors.

(I)

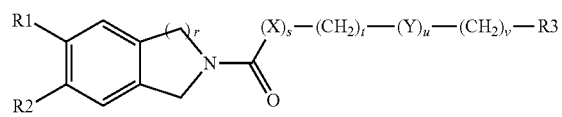

17 Claims, No Drawings

N-SUBSTITUTED TETRAHYDROISOQUINOLINE/ISOINDOLINE HYDROXAMIC ACID COMPOUNDS

This application is a 371 of PCT/EP09/52924 filed Mar. 12, 2009.

FIELD OF APPLICATION OF THE INVENTION

The invention relates to novel N-substituted tetrahydroisoquinoline/isoindoline hydroxamic acid derivatives exhibiting a HDAC 6 antagonistic activity, which have useful pharmaceutical properties and may be used in the preparation of medicaments, particularly against cancer.

TECHNICAL BACKGROUND

Posttranslation modification of proteins is complex and highly regulated with importance for many cellular processes. The reversible modification of lysine residues by acetylation of the ε-amino group has attracted much attention recently (Cohen and Yao, Science STKE, 2004). Initially, the reversible acetylation of N-terminal lysine residues in histone proteins was described (Marks et al., Nat. Rev. Cancer 1, 194-202, 2001). Histone proteins H2A/B, H3 and H4 are forming the octameric histone core complex of chromatin. The complex N-terminal modifications at lysine residues by acetylation or methylation and at serine residues by phosphorylation constitute part of the so called "histone code" (Stahl & Ellis, Nature 403, 41-45, 2000). In a simple model, acetylation of positively charged lysine residues decreases affinity to negatively charged DNA, which now becomes accessible for the entry of transcription factors. Thus, reversible modification of lysine residues within core histone proteins was understood as being important for gene regulation. Histone acetylation and deacetylation is catalysed by histone acetyltransferases (HATs) and histone deacetylases (HDACs), respectively. For example, the HDAC isoenzymes HDAC1 or 2 are associated with transcriptional repressor complexes, switching chromatin to a transcriptionally inactive, silent structure (Marks et al. Nature Cancer Rev 1, 194-202, 2001). The opposite holds true for certain HATs which are associated with transcriptional activator complexes.

Three different classes of HDACs have been described so far, namely class I (HDAC 1-3, 8) with Mr=42-55 and class II (HDAC 4-7, 9, 10) with Mr=120-130 kDa, both sensitive towards inhibition by Trichostatin A (TSA). The class III (Sir2 homologues, SIRTs) enzymes which are quite distinct by their NAD$^+$ dependency and TSA insensitivity (Ruijter et al. Biochem. J. 370, 737-749, 2003; Khochbin et al. Curr. Opin. Gen. Dev. 11, 162-166, 2001; Verdin et al. Trends Gen 19, 286-293, 2003). HDAC 11 with Mr=39 kDa was cloned recently and displayed homology to class I and II family members (Gao et al. J. Biol. Chem. 277, 25748-25755, 2002). Those HATs and HDACs important for transcriptional regulation exist in large complexes together with transcription factor and platform proteins in cells (Fischle et al. Mol. Cell 9, 45-47, 2002). Surprisingly, only about 2% of all genes are regulated by histone acetylation as estimated based on differential display analysis of 340 genes and TSA as the reference HDI (von Lint et al. Gene Expression 5, 245-253, 1996). New studies with the HDAC inhibitor SAHA in multiple myeloma cells showed that these transcriptional changes can be grouped into distinct functional gene classes important for e.g. regulation of apoptosis or proliferation (Mitsiades et al. Proc. Natl. Acad. Sci. 101, pp 540, 2004).

As said before, there is growing evidence for substrates of HDACs different to histone proteins and regulation of processes different to gene transcription (Johnstone & Licht, Cancer Cell 4, 13-18, 2003, Cohen and Yao, Science STKE, 2004). Thus, the correct name for HDACs should be lysine-specific protein deacetylases. As a consequence of these findings, inhibitors of HDACs should not only effect chromatin structure and gene regulation but also protein function and stability by regulating protein acetylation in general. HDAC6 was identified independently in 1999 by Grozinger et al. (Proc. Natl. Acad. Sci. 96, 4868-4873) and Verdel et al. (J. Biol. Chem. 274, 2440-2448) as a HDAC class II enzyme with substrates different to core histone proteins. With 1216 amino acids, HDAC6 is the largest HDAC isoenzyme yet identified in humans and unique with HDAC10 by having two internal ε-acetyllysine specific deacetylation domains, both important for enzymatic activity. HDAC6 is mainly expressed in the cytoplasm and co-localizes with microtubule structures. Microtubles are dynamic structures formed by α/β-tubulin heterodimers, polymerizing parallel to a cylindrical axis. It has long been known that tubulin is modified on lysine residues by acetylation, e.g. lysine residue 40 on α-tubulin, thereby stabilizing tubulin structure and dynamics. HDAC6 was identified as a protein binding to αβ-tubulin, deacetylating α-tubulin and antagonizing the tubulin hyperacetylation induced by tubulin stabilizing anti-cancer agents like taxol (Zhang et al. EMBO J. 22, 1168-1179, 2003; Hubbert et al. Nature 417, 455-458, 2002).

Different publications highlight the pathophysiological importance of HDAC6 in processes like cell migration, protein folding/degradation and apoptosis. In breast cancer, HDAC6 was described as an estrogen induced gene and HDAC6 overexpression enhanced cell migration (Saji et al. Oncogene 2005, 24, 4531-4539). In model experiments, inhibition of HDAC6 by the small molecule inhibitor Tubacin had comparable effect as the anti-estrogen Tamoxifen. Most importantly, Kaplan-Maier analysis of estrogen receptor (ER) positive breast cancer patients showed that those patients with ER and HDAC6 expression responded best to continuous adjuvant treatment with Tamoxifen.

It had been described that Hsp90 is regulated by acetylation and broad class I/II specific HDAC inhibitors like LBH589 induce Hsp90 hyperacetylation (George et al. Blood 105, 1768-76, 2005). The chaperone Hsp90 is well recognized as a key player in stabilization of oncoproteins like mutant raf kinase or overexpressed HER2 receptor tyrosine kinase (Maloney & Workman, Expert Opin. Biol. Ther. 2, 3-24, 2002). The Hsp90 inhibitor 17-allylamino-demethoxy-geldanamycin (17-AAG) is currently tested in clinical phase 1 studies (Ramanathan et al., Clin. Canc. Res. 11, 3385-391, 2005). Kovacs et al. now showed that the acetylated chaperone Hsp90 is a substrate of HDAC6 with deacetylated Hsp90 as the functional ATP binding enzyme in complex with the co-chaperone p23 and the glucocorticoid receptor (Mol. Cell 18, 601-607, 2005). Another function of HDAC6 in protein turnover, namely the clearance of misfolded polyubiquitinylated proteins via the aggresome, was described by Kawaguchi (Cell 115, 727-738, 2003). This interaction is mediated via the C-terminal polyubiquitin associated zinc finger (PAX) domain (Hook et al. Proc. Natl. Acad. Sci. 99, 13425-430, 2002).

Finally, HDAC6 was discussed as a target for chemosensitization towards stabilizing tubulin inhibitors, namely paclitaxel and docetaxel (Marcus et al. Cancer Res. 65, 3883-3893, 2005). This synergism was most pronounced by combination of paclitaxel with the farnesyltransferase inhibitor Sarasar (SCH66336, Ionafarnib). In summary, it is highly likely that, by selective inhibition of HDAC6, various pathological conditions can be treated, in particular cancer.

HDAC inhibitors from various chemical classes were described in the literature with four most important classes, namely (i) hydroxamic acid analogs, (ii) benzamide analogs, (iii) cyclic peptides/peptolides and (iv) fatty acid analogs. A comprehensive summary of known HDAC inhibitors was published recently by Miller et al. (J. Med. Chem. 46, 5097-5116, 2003). There is only limited data published regarding specificity of these histone deacetylase inhibitors. In general, most hydroxamate based HDAC inhibitors are not specific regarding class I and II HDAC enzymes. For example, TSA inhibits HDACs 1, 3, 4, 6 and 10 with $IC_{50}$ values around 20 nM, whereas HDAC8 was inhibited with $IC_{50}$=0.49 µM (Tatamiya et al, AACR Annual Meeting 2004, Abstract #2451). In addition, data on class I selectivity of benzamide HDIs are emerging. The benzamide analog MS-275, developed by Schering AG/Berlex in clinical phase I, inhibited class I HDAC1 and 3 with $IC_{50}$=0.51 µM and 1.7 µM, respectively. In contrast class II HDACs 4, 6, 8 and 10 were inhibited with $IC_{50}$ values of >100 µM, >100 µM, 82.5 µM and 94.7 µM, respectively (Tatamiya et al, AACR Annual Meeting 2004, Abstract #2451). A comprehensive set of pharmacological data is published on these class I or class I/II selective HDAC inhibitors. They are effective directly via induction of histone hyperacetylation on a transcriptional level, up- or down regulating cancer relevant genes. These genes include p21$^{CIP1}$, Cyclin E, transforming growth factor β (TGFβ), p53 or the von Hippel-Lindau (VHL) tumor suppressor genes, which are upregulated, whereas Bcl-XL, bcl2, hypoxia inducible factor (HIF)1α, vascular endothelial growth factor (VEGF) and cyclin A/D are down-regulated by HDAC inhibition (reviewed by Kramer et al. Trends Endocrin. Metabol. 12, 294-300, 2001).

Interestingly, only very few data is published describing isotype-selective HDAC inhibitors.

The group of S. Schreiber described a hydroxamate analog named Tubacin as a selective HDAC6 inhibitor (Haggarty et al. Proc. Natl. Acad. Sci. USA 100, 4389-4394, 2003). In initial experiments Tubacin induced tubulin hyperacetylation and decreased cell migration. Therefore, a pharmacological activity of an HDAC6 selective inhibitor in treating advanced cancer patients with metastatic disease is highly likely.

There is growing rational for synergism of class I and class I/II specific HDAC inhibitors with chemotherapeutic as well as target specific cancer drugs. For example, synergism was shown for SAHA with the kinase/cdk inhibitor flavopiridol (Alemenara et al. Leukemia 16, 1331-1343, 2002), for LAQ-824 with the bcr-abl kinase inhibitor Glivec in CML cells (Nimmanapalli et al. Cancer Res. 63, 5126-5135, 2003), for SAHA and Trichostatin A (TSA) with etoposide (VP16), cisplatin and doxorubicin (Kim et al. Cancer Res. 63, 7291-7300, 2003) and LBH589 with the Hsp90 inhibitor 17-AAG (George et al. Blood 105, 1768-76, 2005). It is highly likely that a selective HDAC6 inhibitor also synergizes with established chemotherapeutic as well as targeted cancer drugs, e.g. taxanes or epothilones as tubulin stabilizing agents.

Clinical studies in cancer with class I and class I/II selective HDAC inhibitors are on-going, namely with SAHA (Merck Inc.), Valproic acid, FK228/Depsipeptide (Gloucester Pharmaceuticals/NCI), MS275 (Berlex-Schering), NVP LBH-589 (Novartis), PXD-101 (Topotarget/Curagen), MGCD0103 (Methylgene Inc), Valproic acid (G2M Cancer Drugs/Topotarget) and Pivaloyloxymethylbutyrate/Pivanex (Titan Pharmaceuticals). These studies showed first evidence of clinical efficacy, highlighted recently by partial and complete responses with FK228/Depsipeptide in patients with peripheral T-cell lymphoma (Plekarz et al. Blood, 98, 2865-2868, 2001). To our knowledge, no clinical development of an isotype-selective HDAC inhibitor has been reported so far.

Recent publications showed possible medical use of class I/II specific HDAC inhibitors in diseases different to cancer. These diseases include systemic lupus erythematosus (Mishra et a. J. Clin. Invest. 111, 539-552, 2003; Reilly et al. J. Immunol. 173, 4171-4178, 2004), rheumatoid arthritis (Chung et al. Mol, Therapy 8, 707-717, 2003; Nishida et al. Arthritis & Rheumatology 50, 3365-3376, 2004), inflammatory diseases (Leoni et al. Proc. Natl. Acad. Sci. USA 99, 2995-3000, 2002) and neurodegenerative diseases like Huntington's disease (Steffan et al. Nature 413, 739-743, 2001, Hockly et al. Proc. Natl. Acad. Sci. USA 100(4):2041-6, 2003). It is likely that isotype selective inhibitors are also pharmacologically active in these diseases. As such, HDAC6 has been described as a factor in the organization of the T-cell receptor/antigen presenting cell immune synapse (Serrador et al. Immunity 20, 417-428, 2004).

Cancer chemotherapy was established based on the concept that cancer cells with uncontrolled proliferation and a high proportion of cells in mitosis are killed preferentially. Standard cancer chemotherapeutic drugs finally kill cancer cells upon induction of programmed cell death ("apoptosis") by targeting basic cellular processes and molecules, namely RNA/DNA (alkylating and carbamylating agents, platin analogs and topoisomerase inhibitors), metabolism (drugs of this class are named anti-metabolites) as well as the mitotic spindle apparatus (stabilizing and destabilizing tubulin inhibitors). Class I and class I/II selective inhibitors of histone deacetylases constitute a new class of anti cancer drugs with differentiation and apoptosis inducing activity. It is highly likely that isotype selective inhibitors have a defined activity profile and a broad therapeutic index. In this regard HDAC6 selective inhibitors might be active in cancer therapy by, for example, inhibiting cell migration, synergizing with agents targeting the mitotic spindle or effecting dysregulated protein folding and degradation via the chaperone and proteasome/aggresome machineries.

STATE OF THE ART

HDAC inhibitors are in general known in the art. WO 2005/108367 describes some N-substituted-1,2,34-tetrahydroisoquinoline hydroxamic acid compounds as pharmaceutically active compounds. However, WO 2005/108367 does not mention the above described different isotypes of the HDAC enzymes and a potential isotype selectivity of the compounds disclosed therein.

HDAC 6 itself is described in literature as a target structure for the treatment of different pathophysiological states:

WO 2005/078081 is directed to the use of a compound that regulates, inhibits or activates the tubulin deacetylase activity of HDAC 6 for the prophylaxis and treatment of patients suffering from alterations in the immunological system, preferably from an altered T-lymphocyte activation.

In WO 2006/111596, the use of HDAC 6 agonistic compounds that activate the tubulin deacetylase activity of HDAC 6 for the treatment of viral infections is disclosed.

WO 2007/147868 describes the treatment of muscle atrophy using HDAC 6 inhibitors such as antisense oligonucleotides, antibodies, aptamers, competitive peptides and non-specific HDAC inhibitors like TSA and SAHA as well as down-regulation of the HDAC 6 gene by way of RNA interference.

WO 2007/130429 is directed to novel selective HDAC 6 inhibitors all containing a 1,3-dioxane core used in a method for treating a proliferative disorder, like cancer or an inflammatory disease, and in a method for treating a degradation disorder, like a protein deposition disorder or a neurodegenerative disorder.

US 2007/0207950 discloses methods for inhibiting Hsp90 activity and for modulating steroid receptor signaling in cells as well as methods for treating cancer associated with Hsp90 and a disorder associated with aberrant steroid receptor signaling like cancer, muscle atrophy and others, utilizing HDAC 6 inhibitors. Said HDAC 6 inhibitors inter alia comprise hydroxamic acid based compounds like TSA and SAHA, cyclic-hydroxamic-acid-containing peptides (CHAPS) as well as further art known substances.

Nevertheless, there remains a need in the art for new, well-tolerated and efficacious isotype-selective inhibitors of the HDAC enzymes.

DESCRIPTION OF THE INVENTION

It has now been found that the tetrahydroisoquinoline/isoindoline hydroxamic acid derivatives, which are described in greater detail below, are inhibitors of histone deactylases (HDAC), in particular they are selective inhibitors of HDAC 6.

The invention thus relates in a first embodiment to compounds of formula I:

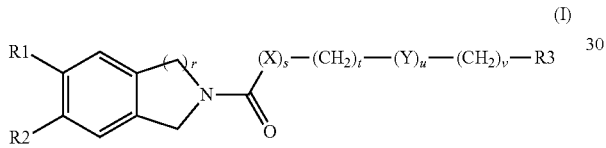

wherein
one of R1 and R2 is H and the other is

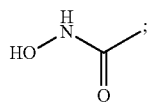

R3 is hydrogen, —OR4, —NR5R6, an optionally substituted alicyclic, heteroalicyclic, aromatic or heteroaromatic radical, wherein
the alicyclic radical is a 3- to 6-membered monocyclic group,
the heteroalicyclic radical is a 5- to 6-membered monocyclic group comprising one or two heteroatoms, each of which is selected from the group consisting of nitrogen, oxygen and sulfur,
the aromatic radical is phenyl or naphthyl,
the heteroaromatic radical is a 5- to 6-membered monocyclic group or a 9- to 10-membered bicyclic group comprising one or two heteroatoms, each of which is selected from the group consisting of nitrogen, oxygen and sulfur, and
the substituents of the optionally substituted alicyclic, heteroalicyclic, aromatic or heteroaromatic radical are halogen, 1-4C alkyl, 1-4C alkoxy or phenyl;
R4 is hydrogen, 1-4C alkyl or a substituted or unsubstituted alicyclic, heteroalicyclic, aromatic or heteroaromatic group, wherein each of these groups is as defined as in R3;
R5 and R6 are each independently H or 1-4C alkyl;
X is a single bond, —CH=CH—, —C≡C—, —NH—, oxygen or sulfur;
Y is —NH—, oxygen or sulfur;
r is 1 or 2,
one of s and u is 0 and the other is 1,
t is 0, 1, 2, 3, 4 or 5, and
v is 0, 1, 2, 3 or 4;
and the salts, solvates and hydrates of these compounds.

In a preferred embodiment the present invention relates to a compound of formula I
wherein
t is 0 or 1,
v is 0, 1 or 2 and
the remaining substituents and indices are as defined in the first embodiment;
and the salts, solvates and hydrates of these compounds.

In a further preferred embodiment the present invention relates to a compound of formula I
wherein
s is 1,
t is 1,
u is 0,
v is 0, 1 or 2, and
the remaining substituents and indices are as defined in the first embodiment;
and the salts, solvates and hydrates of these compounds.

In another further preferred embodiment the present invention relates to a compound of formula I
wherein
S is 0,
t is 1,
u is 1 and
v is 0, 1 or 2, and
the remaining substituents and indices are as defined in the first embodiment;
and the salts, solvates and hydrates of these compounds.

In a more preferred embodiment the present invention relates to a compound of formula I
wherein
R3 is hydrogen, —OR4, —NR5R6, an optionally substituted alicyclic, heteroalicyclic, aromatic or heteroaromatic radical, wherein
the alicyclic radical is selected from the group consisting of cyclopropyl and cyclobutyl,
the heteroalicyclic radical is tetrahydrofuryl,
the aromatic radical is phenyl,
the heteroaromatic radical is selected from the group consisting of imidazolyl, pyridyl, indolyl and quinolinyl and
the substituents of the optionally substituted alicyclic, heteroalicyclic, aromatic or heteroaromatic radical are selected from the group consisting of —CH₃, —OCH₃ or phenyl;
R4 is —CH₃ or phenyl;
R5 and R6 are each independently H or —CH₃;
Y is oxygen;
s is 0,
u is 1 and
the remaining substituents and indices are as defined in the first embodiment;
and the salts, solvates or hydrates of these compounds.

In another more preferred embodiment the present invention relates to a compound of formula I
wherein
R3 is hydrogen, —OR4, —NR5R6, an optionally substituted alicyclic, heteroalicyclic, aromatic or heteroaromatic radical, wherein
the alicyclic radical is selected from the group consisting of cyclopropyl and cyclobutyl,
the heteroalicyclic radical is tetrahydrofuryl,
the aromatic radical is phenyl, the heteroaromatic radical is selected from the group consisting of imidazolyl, pyridyl, indolyl and quinolinyl and the substituents of the optionally substituted alicyclic, heteroalicyclic, aromatic or heteroaromatic radical are selected from the group consisting of —CH₃, —OCH₃ or phenyl;

R4 is —CH₃ or phenyl;

R5 and R6 are each independently H or —CH₃;

X is a single bond, —C≡C—, —NH—, or oxygen;

s is 1, u is 0 and the remaining substituents and indices are as defined in the first embodiment;

and the salts, solvates or hydrates of these compounds.

In a further more preferred embodiment the present invention relates to a compound of formula I wherein r is 1 and the remaining substituents and indices are as defined in the first embodiment;

and the salts, solvates or hydrates of these compounds.

In another further more preferred embodiment the present invention relates to a compound of formula I wherein R1 is

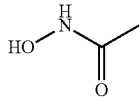

and R2 is H, r is 2 and the remaining substituents and indices are as defined in the first embodiment;

and the salts, solvates or hydrates of these compounds.

In a most preferred embodiment the present invention relates to a compound of formula I selected from:

1. N-Hydroxy-2-(indol-3-ylacetyl)-1,2,3,4-tetrahydroisoquinoline-6-carboxamide
2. N-Hydroxy-2-(pyridin-2-ylacetyl)-1,2,3,4-tetrahydroisoquinoline-6-carboxamide,
3. 2-(Cyclobutylcarbonyl)-N-hydroxy-1,2,3,4-tetrahydroisoquinoline-6-carboxamide,
4. N6-Hydroxy-N2-methyl-3,4-dihydroisoquinoline-2,6(1H)-dicarboxamide,
5. N6-Hydroxy-N2-(3-methoxypropyl)-3,4-dihydroisoquinoline-2,6(1H)-dicarboxamide,
6. 3-Methoxypropyl-6-(hydroxycarbamoyl)-3,4-dihydroisoquinoline-2(1H)-carboxylate,
7. N-Hydroxy-2-(3-pyridin-3-ylpropanoyl)-1,2,3,4-tetrahydroisoquinoline-6-carboxamide,
8. N-Hydroxy-2-(pyridin-3-ylacetyl)-1,2,3,4-tetrahydroisoquinoline-6-carboxamide,
9. 2-[4-(Dimethylamino)butanoyl]-N-hydroxy-1,2,3,4-tetrahydroisoquinoline-6-carboxamide,
10. N-Hydroxy-2-[(2-methyl-1H-imidazol-1-yl)acetyl]-1,2,3,4-tetrahydroisoquinoline-6-carboxamide,
11. N-Hydroxy-2-[(2-methoxyethoxy)acetyl]-1,2,3,4-tetrahydroisoquinoline-6-carboxamide,
12. 2-Acetyl-N-hydroxy-1,2,3,4-tetrahydroisoquinoline-6-carboxamide,
13. N-Hydroxy-2-(tetrahydrofuran-3-ylcarbonyl)-1,2,3,4-tetrahydroisoquinoline-6-carboxamide,
14. N-Hydroxy-2-(pyridin-2-ylacetyl)-1,2,3,4-tetrahydroisoquinoline-6-carboxamide,
15. N-Hydroxy-2-[(5-methoxy-1H-indol-2-yl)carbonyl]-1,2,3,4-tetrahydroisoquinoline-6-carboxamide,
16. N-Hydroxy-2-(cyclopropylcarbonyl)-1,2,3,4-tetrahydroisoquinoline-6-carboxamide,
17. 2-But-2-ynoyl-N-hydroxy-1,2,3,4-tetrahydroisoquinoline-7-carboxamide,
18. N-Hydroxy-2-(1H-indol-3-ylacetyl)-1,2,3,4-tetrahydroisoquinoline-7-carboxamide,
19. N-Hydroxy-2-(pyridin-3-ylacetyl)-1,2,3,4-tetrahydroisoquinoline-7-carboxamide,
20. N-Hydroxy-2-(tetrahydrofuran-3-ylcarbonyl)-1,2,3,4-tetrahydroisoquinoline-7-carboxamide,
21. N-Hydroxy-2-(pyridin-2-ylacetyl)-1,2,3,4-tetrahydroisoquinoline-7-carboxamide,
22. N7-Hydroxy-N2-(2-phenylethyl)-3,4-dihydroisoquinoline-2,7(1H)-dicarboxamide,
23. N-Hydroxy-2-(4-methylbenzoyl)-1,2,3,4-tetrahydroisoquinoline-7-carboxamide,
24. N-Hydroxy-2-[(5-methoxy-1H-indol-2-yl)carbonyl]-1,2,3,4-tetrahydroisoquinoline-7-carboxamide,
25. 2-Acetyl-N-hydroxy-1,2,3,4-tetrahydroisoquinoline-7-carboxamide,
26. Pyridin-3-ylmethyl 5-(hydroxycarbamoyl)-1,3-dihydro-2H-isoindole-2-carboxylate,
27. N-Hydroxy-2-(quinolin-2-ylcarbonyl)isoindoline-5-carboxamide,
28. N-Hydroxy-2-(quinolin-6-ylcarbonyl)isoindoline-5-carboxamide,
29. N-Hydroxy-2-(isoquinolin-3-ylcarbonyl)isoindoline-5-carboxamide,
30. 2-(Biphenyl-4-ylcarbonyl)-N-hydroxyisoindoline-5-carboxamide,
31. N-Hydroxy-2-(3-pyridin-3-ylpropanoyl)-1,2,3,4-tetrahydroisoquinoline-7-carboxamide,
32. N7-Hydroxy-N2-(3-methoxypropyl)-3,4-dihydroisoquinoline-2,7(1H)-dicarboxamide,
33. 2-[4-(Dimethylamino)butanoyl]-N-hydroxy-1,2,3,4-tetrahydroisoquinoline-7-carboxamide,
34. 3-Methoxypropyl 7-(hydroxycarbamoyl)-3,4-dihydroisoquinoline-2(1H)-carboxylate,
35. N7-Hydroxy-N2-methyl-3,4-dihydroisoquinoline-2,7(1H)-dicarboxamide,
36. 2-(Cyclobutylcarbonyl)-N-hydroxy-1,2,3,4-tetrahydroisoquinoline-7-carboxamide,
37. N-Hydroxy-2-(1H-indol-5-ylcarbonyl)-1,2,3,4-tetrahydroisoquinoline-7-carboxamide,
38. N-Hydroxy-2-[(2-methoxyethoxy)acetyl]-1,2,3,4-tetrahydroisoquinoline-7-carboxamide,
39. N-Hydroxy-2-[3-(2-methyl-1H-imidazol-1-yl)propanoyl]-1,2,3,4-tetrahydroisoquinoline-7-carboxamide,
40. Benzyl 6-(hydroxycarbamoyl)-3,4-dihydroisoquinoline-2(1H)-carboxylate,
41. N-Hydroxy-2-(phenoxyacetyl)-1,2,3,4-tetrahydroisoquinoline-6-carboxamide,
42. N-Hydroxy-2-(4-methylbenzoyl)-1,2,3,4-tetrahydroisoquinoline-6-carboxamide,
43. N6-Hydroxy-N2-[2-(1H-indol-3-yl)ethyl]-3,4-dihydroisoquinoline-2,6(1H)-dicarboxamide,
44. N6-Hydroxy-N2-benzyl-3,4-dihydroisoquinoline-2,6(1H)-dicarboxamide,
45. N6-Hydroxy-N2-(2-phenoxyethyl)-3,4-dihydroisoquinoline-2,6(1H)-dicarboxamide and
46. N-hydroxy-2-(1H-Indol-5-ylcarbonyl)-1,2,3,4-tetrahydroisoquinoline-6-carboxamide or salts thereof, particularly the hydrochlorides of these compounds.

The present invention further relates to a pharmaceutical composition comprising a compound of formula I according to the above embodiments or a pharmaceutically acceptable salt thereof together with customary pharmaceutical excipients.

In a preferred embodiment this pharmaceutical composition comprises a further active ingredient, most preferably an anti-cancer drug.

The present invention further relates to a compound of formula I according to the above embodiments or a pharmaceutically acceptable salt thereof or a pharmaceutical composition containing either entity for use in a method for the treatment of the human body by therapy.

The present invention further relates to a compound of formula I according to the above embodiments or a pharmaceutically acceptable salt thereof or a pharmaceutical composition containing either entity for use in the treatment of diseases responsive or sensitive to the inhibition of the activity of HDAC6.

In a preferred embodiment the present invention relates to a compound of formula I according to the above embodiments or a pharmaceutically acceptable salt thereof or a pharmaceutical composition containing either entity for use in the treatment of a benign and/or a malignant neoplasia, such as e.g. cancer.

The present invention further relates to a use of compounds of formula I according to the above embodiments for the manufacture of pharmaceutical compositions for treating diseases different to malignant neoplasia, including
(i) arthropathies and osteopathological conditions or diseases such as rheumatoid arthritis, osteoarthritis, gout, polyarthritis, and psoriatic arthritis;
(ii) autoimmune diseases like systemic lupus erythematosus and transplant rejection;
(iii) hyperproliferative diseases such as smooth muscle cell proliferation including vascular proliferative disorders, atherosclerosis, restenosis;
(iv) fibro-proliferative diseases such as lung fibrosis, systemic sclerosis and scleroderma, retroperitoneal fibrosis, nephrogenic systemic fibrosis, renal fibrosis, hepatic fibrosis, cardiac fibrosis, chronic kidney disease and polycystic kidney disease;
(v) acute and chronic inflammatory conditions or diseases and dermal conditions such as psoriasis, ulcerative colitis, Crohn's disease, chronic pancreatitis, hepatitis, liver cirrhosis, allergic rhinitis, allergic dermatitis, cystic fibrosis, chronic obstructive bronchitis, chronic obstructive pulmonary disease (COPD) and asthma;
(vi) endometriosis, uterine fibroids, endometrial hyperplasia, fatty liver disease, non-alcoholic steato-hepatitis and benign prostate hyperplasia;
(vii) cardiac dysfunction such as diastolic heart failure;
(viii) inhibiting immunosuppressive conditions like HIV infections;
(ix) neuropathological disorders like Multiple Sclerosis, Parkinsons disease, Alzheimers disease, Huntingtons disease or polyglutamine related disorders;
(x) pathological conditions amenable to treatment by potentiating of endogenous gene expression as well as enhancing transgene expression in gene therapy;
(xi) muscle dystrophy with Duchenne's muscular dystrophy as one example;
(xii) various forms of diabetes, including insulin resistant type 2 diabetes; and
(xiii) interstitial lung diseases like idiopathic pulmonary fibrosis, asbestosis, Bleomycin—or Busulfan—induced lung fibrosis.

The present invention further relates to a method for treating a disease responsive or sensitive to the inhibition of the activity of HDAC6 in a patient comprising administering to said patient a therapeutically effective and tolerable amount of a compound of formula I according to the above embodiments or a pharmaceutically acceptable salt thereof.

In a preferred embodiment the disease to be treated is a benign and/or a malignant neoplasia, such as e.g. cancer and the compound of formula I or its pharmaceutically acceptable salts are administered simultaneously, sequentially or separately with one or more further therapeutic agents.

1-4C-Alkyl represents a straight-chain or branched alkyl radical having 1 to 4 carbon atoms. Examples which may be mentioned are the butyl, isobutyl, sec-butyl, tert-butyl, propyl, isopropyl and preferably the ethyl and methyl radicals.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

The 3- to 6-membered monocyclic alicyclic radical includes cyclopropyl, cyclobutyl, cyclopentyl and cyclohexyl.

The 5- to 6-membered monocyclic heteroalicyclic radical comprising one or two heteroatoms, each of which is selected from the group consisting of nitrogen, oxygen and sulfur, includes, without being restricted thereto, pyrrolidinyl, pyrazolidinyl, imidazolidinyl, tetrahydrofuranyl, oxazolidinyl, isoxazolidinyl, tetrahydrothienyl, thiazolidine, piperidinyl, piperazinyl, tetrahydropyranyl, dioxanyl, morpholinyl, thianyl, dithianyl and thiomorpholinyl.

The 5- to 6-membered monocyclic and the 9- to 10-membered bicyclic heteroaromatic radical comprising one or two heteroatoms, each of which is selected from the group consisting of nitrogen, oxygen and sulfur, include, without being restricted thereto, thienyl, furanyl, pyrrolyl, oxazolyl, isoxazolyl, pyrazolyl, imidazolyl, thiazolyl, isothiazolyl, triazolyl, oxadiazolyl, thiadiazolyl, pyridinyl, pyrimidinyl, pyrazinyl or pyridazinyl; and, in particular, the stable benzo-fused derivatives thereof, such as e.g. benzothiophenyl, benzofuranyl, indolyl, benzoxazolyl, benzothiazolyl, indazolyl, benzimidazolyl, benzisoxazolyl, benzisothiazolyl, benzofurazanyl, quinolinyl, isoquinolinyl, quinazolinyl, quinoxalinyl, phthalazinyl or cinnolinyl; and purinyl, indolizinyl, naphthyridinyl or pteridinyl.

In particular these exemplary radicals may include imidazol-1-yl, pyridine-2-yl, pyridine-3-yl, indol-2-yl, indol-3-yl, indol-5-yl, quinolin-2-yl and quinolin-6-yl.

Compounds according to the present invention are selective HDAC 6 inhibitors; in this context "selective" means that they inhibit isotype 6 of the HDAC enzymes at a concentration ($IC_{50}$) that is at least 10 times lower than that needed for the inhibition of any other HDAC isotype.

Salts of compounds of the formula I can be—depending on substitution—acid addition salts or salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid such as (−)-L-malic acid or (+)-D-malic acid, fumaric acid, succinic acid, oxalic acid, tartaric acid such as (+)-L-tartaric acid or (−)-D-tartaric acid or meso-tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

In the context of the foregoing, as further acids, which may be used in the preparation of possible salts of compounds of formula I, can be mentioned any selected from adipic acid, L-ascorbic acid, L-aspartic acid, benzenesulfonic acid, 4-acetamido-benzoic acid, (+)-camphoric acid, (+)-camphor-10-sulfonic acid, caprylic acid (octanoic acid), dodecylsulfonic acid, ethane-1,2-disulfonic acid, ethanesulfonic acid, 2-hydroxy-ethanesulfonic acid, formic acid, galactaric acid, gentisic acid, D-glucoheptonic acid, D-glucuronic acid, glutamic acid, 2-oxo-glutaric acid, hippuric acid, lactic acid such as D-lactic acid or L-lactic acid, malonic acid, mandelic acid such as (+)-mandelic acid or (−)-mandelic acid, naphthalene-1,5-disulfonic acid, naphthalene-2-sulfonic acid, nicotinic acid, palmitic acid, pyroglutamic acid such as L-pyroglutamic acid, hydroiodic acid, cyclamic acid, thiocyanic acid, 2,2-dichloroacetic acid, glycerophosphoric acid, 1-hydroxy-2-naphthoic acid, salicyclic acid, 4-aminosalicyclic acid, glycolic acid, oleic acid, glutaric acid, cinnamic acid, capronic acid, isobutyric acid, propionic acid, capric acid, undecylenic acid and orotic acid.

On the other hand, salts of the hydoxamic acids according to the present invention with bases are—depending on substitution—also suitable. As examples of salts with bases are mentioned the lithium, sodium, potassium, calcium, aluminium, magnesium, titanium, ammonium, meglumine or guanidinium salts. Here, too, the bases being employed in salt preparation can be used in an equimolar quantitative ratio or one differing therefrom.

Pharmacologically intolerable salts, which can be obtained, for example, as process products during the preparation of the compounds according to the invention on an industrial scale, can be converted into pharmacologically tolerable salts by processes known to the person skilled in the art.

According to expert's knowledge the compounds of formula I of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

In one embodiment of this invention, salts of the compounds of formula I include salts of compounds of formula I with hydrochloric acid.

The compounds according to the present invention can be prepared, for example, as shown in the reaction schemes below and according to the reaction steps specified as follows, or, particularly, in a manner as described by way of example in the following examples, or analogously or similarly thereto using preparation procedures and synthesis strategies known to the person skilled in the art.

In reaction scheme 1 the formation of the isoindoline moiety is shown. After radical bromination reaction under typical radical formation conditions, like N-bromosuccinimide, and a radical starter, like AIBN, the dibromo compound (VI) is obtained from a suitable solvent. Subsequent ring closure with benzyl amine and amine cleavage using benzyl chloroformate (Z—Cl) lead to compound (IV). Saponification of the methyl ester under basic nucleophilic conditions gives then the carboxylic acid compound (III).

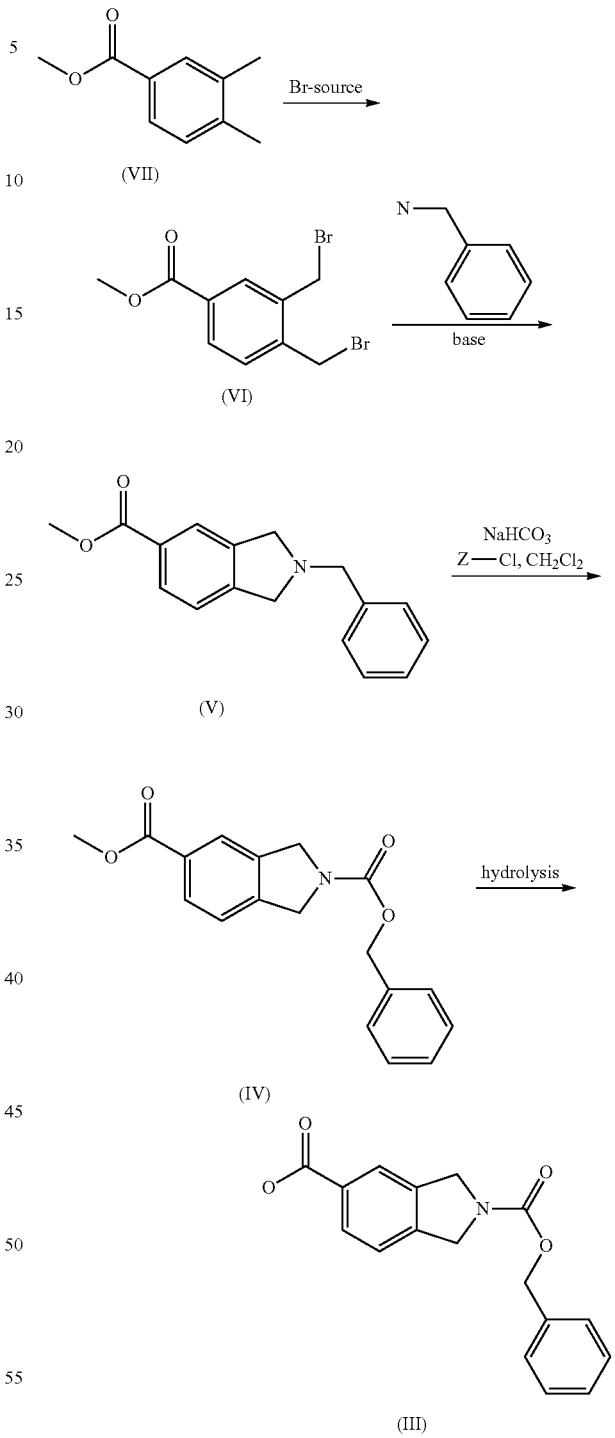

Reaction scheme 2 describes the formation of the methyl ester of the 7-carboxy-1,2,3,4-tetrahydroisoquinoline moiety, which is done under conditions using MeOH, Boc2O and nitro methane. Subsequently, deprotection under acidic conditions, like trifluoroacetic acid, and reaction with benzyl chloroformate (Z—Cl) give compound (IX). Saponification of the methyl ester under basic nucleophilic conditions leads then to the carboxylic acid compound (VIII).

Reaction scheme 2

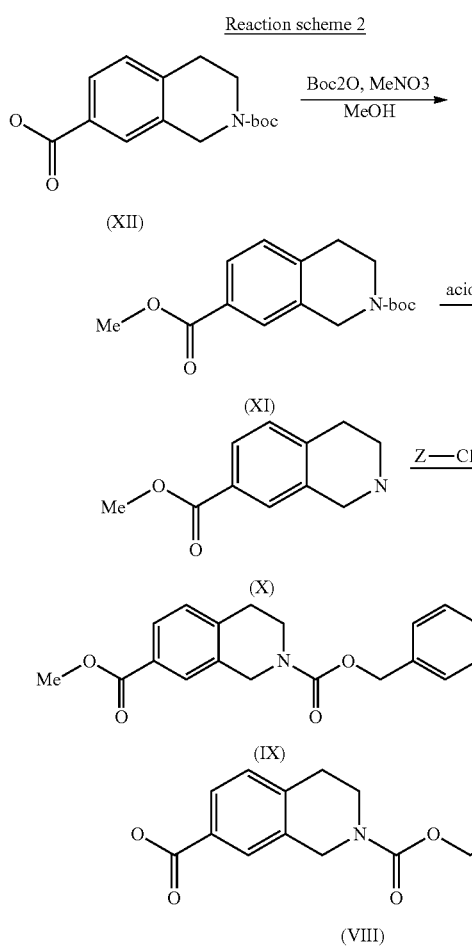

Reaction scheme 3 shows the reaction of the methylester of 6-carboxy-1,2,3,4-tetrahydroisoquinoline (compound (XIV)) with benzyl chloroformate (Z—Cl) and the saponification of the methyl ester under basic nucleophilic conditions to obtain the carboxylic acid compound (XIII).

Reaction scheme 3

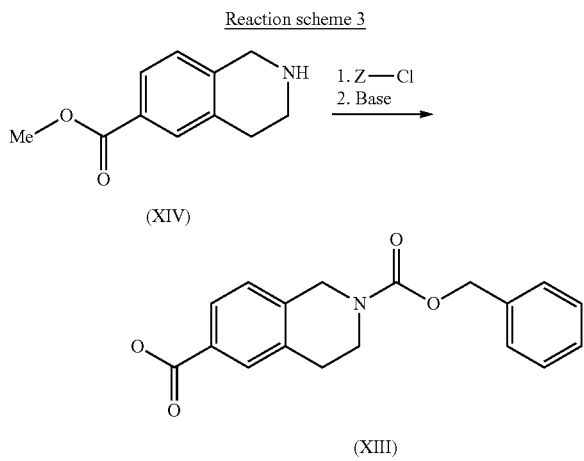

In the subsequent reaction sequence compounds (III), (VIII) and (XIII) are coupled under typical coupling conditions like EDC and HOBt with a protected hydroxylamine derivative, e.g. a THP-group protected hydroxylamine derivative, and the benzyloxycarbonyl group is removed under typical reductive conditions, like using hydrogen and a Pd/C catalyst, to obtain the respective secondary amine.

In the next step (reaction scheme 4), the obtained secondary amine compounds (displayed as general formula (II), wherein
one of R1' and R2' is H and the other is and r $$\text{THP} - \text{O} - \overset{H}{\underset{\underset{O}{\|}}{N}} - \text{CH}_3$$

is 0 or 1) are coupled with an acid chloride compound under typical coupling conditions to give the respective protected N-substituted tetrahydroisoquinoline/isoindoline compound. The following de-protection of the THP-protection group under typical acidic conditions gives the final compounds displayed as general formula (I), wherein the substituents and indices are as defined above.

Reaction scheme 4

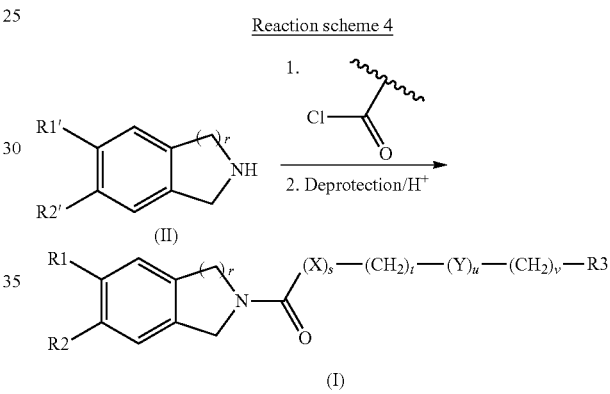

The above protective groups and methods may be also those mentioned in "Protective Groups in Organic Synthesis" by T. Greene and P. Wuts (John Wiley & Sons, Inc. 1999, 3rd Ed.) or in "Protecting Groups" (Thieme Foundations of Organic Chemistry Series) by P. Kocienski (Thieme Medical Publishers, 2000).

The following examples serve to illustrate the invention further without restricting it.

EXAMPLES

1. N-Hydroxy-2-(indol-3-ylacetyl)-1,2,3,4-tetrahydroisoquinoline-6-carboxamide hydrochloride 180 mg 2-(1H-indol-3-ylacetyl)-N-(tetrahydro-2H-pyran-2-yloxy)-1,2,3,4-tetrahydroisoquinoline-6-carboxamide are dissolved in methanol and 6 ml of a solution of 0.1 M HCl in water are added drop wise. The mixture is stirred overnight. The mixture is evaporated in vacuo and the residue is treated with a mixture of water and acetonitrile and lyophilized. 92 mg (63%) of the title compound are obtained. MH+=350.0

2. N-Hydroxy-2-(pyridin-2-ylacetyl)-1,2,3,4-tetrahydroisoquinoline-6-carboxamide hydrochloride A mixture of 75 mg 2-(pyridin-2-ylacetyl)-N-(tetrahydro-2H-pyran-2-yloxy)-1,2,3,4-tetrahydroisoquinoline-6-carboxamide and 6 ml of a 0.1M solution of HCl in water in 4 ml methanol is stirred overnight at ambient temperature and evaporated. The mixture is dissolved in a mixture of 2 ml water and 2 ml acetonitrile and lyophilized. 75 mg of the title compound are obtained as colorless solid. MH+=312.1

3. 2-(Cyclobutylcarbonyl)-N-hydroxy-1,2,3,4-tetrahydroisoquinoline-6-carboxamide 160 mg of 2-(cyclobutylcarbonyl)-N-(tetrahydro-2H-pyran-2-yloxy)-1,2,3,4-tetrahydroisoquinoline-6-carboxamide and 2 ml of a 0.1M solution of HCl in water in 2 ml methanol are stirred overnight at ambient temperature. The reaction mixture is evaporated and the residue is treated with acetonitrile. 53 mg of nearly colorless crystals are obtained. MH+=275.1

4. N6-Hydroxy-N2-methyl-3,4-dihydroisoquinoline-2,6(1H)-dicarboxamide

A mixture of 110 mg N2-methyl-N6-(tetrahydro-2H-pyran-2-yloxy)-3,4-dihydroisoquinoline-2,6(1H)-dicarboxamide in 4 ml methanol and 6 ml 0.1M aqueous HCl is stirred for 16 h and evaporated. The residue is dissolved in acetonitrile and water and lyophilized. 85 mg of colorless foam are obtained. MH+=250.2

5. N6-Hydroxy-N2-(3-methoxypropyl)-3,4-dihydroisoquinoline-2,6(1H)-dicarboxamide A mixture of 180 mg of N2-(3-methoxypropyl)-N6-(tetrahydro-2H-pyran-2-yloxy)-3,4-dihydroisoquinoline-2,6 (1H)-dicarboxamide in 4 ml methanol and 6 ml of an aqueous 0.1 N HCl is stirred overnight at ambient temperature and evaporated. The residue is dissolved in acetonitrile and water and lyophilized. 115 mg of the title compound are obtained. MH+=308.2

6. 3-Methoxypropyl-6-(hydroxycarbamoyl)-3,4-dihydroisoquinoline-2(1H)-carboxylate A mixture of 90 mg 3-methoxypropyl 6-[(tetrahydro-2H-pyran-2-yloxy)carbamoyl]-3,4-dihydroisoquinoline-2(1H)-carboxylate in 1 ml methanol and 1.5 ml aqueous HCl (0.1 N) is stirred for 3 h at ambient temperature. The reaction mixture is lyophilized. 71.4 mg of a colorless solid are obtained. MH+=309.0

7. N-Hydroxy-2-(3-pyridin-3-ylpropanoyl)-1,2,3,4-tetrahydroisoquinoline-6-carboxamide hydrochloride A mixture of 140 mg of 2-(3-pyridin-3-ylpropanoyl)-N-(tetrahydro-2H-pyran-2-yloxy)-1,2,3,4-tetrahydroisoquinoline-6-carboxamide, 1 ml methanol and 1.5 ml of an aqueous, 0.1 M HCl are stirred for 3 h. Additional 2 ml of a 2N aqueous HCl are added and the mixture is stirred overnight. The mixture is lyophilized. 117 mg of the title compound are obtained as colorless oil. MH+=326.1

8. N-Hydroxy-2-(pyridin-3-ylacetyl)-1,2,3,4-tetrahydroisoquinoline-6-carboxamide hydrochloride A mixture of 50 mg 2-(3-pyridin-3-ylpropanoyl)-N-(tetrahydro-2H-pyran-2-yloxy)-1,2,3,4-tetrahydroisoquinoline-6-carboxamide, 1 ml methanol and 1.5 ml 0.1 M aqueous hydrochloric acid are stirred for 3 h at ambient temperature. The reaction mixture is lyophilized. 70 mg of the title compound are obtained as colorless solid. MH+=312.1

9. 2-[4-(Dimethylamino)butanoyl]-N-hydroxy-1,2,3,4-tetrahydroisoquinoline-6-carboxamide hydrochloride A mixture of 35 mg 2-[4-(dimethylamino)butanoyl]-N-(tetrahydro-2H-pyran-2-yloxy)-1,2,3,4-tetrahydroisoquinoline-6-carboxamide, 1 ml methanol and 1.5 ml 0.1N aqueous HCl is stirred for 3 h at ambient temperature. Subsequently, the mixture is lyophilized. 40 mg of a colorless solid are obtained. MH+=306.1

10. N-Hydroxy-2-[(2-methyl-1H-imidazol-1-yl)acetyl]-1,2,3,4-tetrahydroisoquinoline-6-carboxamide hydrochloride A mixture of 18 mg 2-[(2-methyl-1H-imidazol-1-yl)acetyl]-N-(tetrahydro-2H-pyran-2-yloxy)-1,2,3,4-tetrahydroisoquinoline-6-carboxamide, 1 ml methanol and 1.5 ml 0.1N aqueous HCl is stirred for 3 h at ambient temperature. The reaction mixture is then lyophilized. 18 mg of the title compound are obtained as colorless solid. MH+=329.1

11. N-Hydroxy-2-[(2-methoxyethoxy)acetyl]-1,2,3,4-tetrahydroisoquinoline-6-carboxamide A mixture of 110 mg 2-[(2-methoxyethoxy)acetyl]-N-(tetrahydro-2H-pyran-2-yloxy)-1,2,3,4-tetrahydroisoquinoline-6-carboxamide, 1 ml methanol and 1.5 ml 0.1N aqueous hydrochloric acid are stirred for 3 h at ambient temperature. Subsequently, the mixture is lyophilized. 85 mg of the title compound are obtained as colorless oil. MH+=309.1

12. 2-Acetyl-N-hydroxy-1,2,3,4-tetrahydroisoquinoline-6-carboxamide

A mixture of 150 mg of 2-acetyl-N-(tetrahydro-2H-pyran-2-yloxy)-1,2,3,4-tetrahydroisoquinoline-6-carboxamide, 1 ml methanol and 1.5 ml of an aqueous, 0.1 N hydrochloric acid is stirred for 3 h at ambient temperature. The reaction mixture is lyophilized. 40 mg of the title compound are obtained as colorless oil. MH+=235.0

13. N-Hydroxy-2-(tetrahydrofuran-3-ylcarbonyl)-1,2,3,4-tetrahydroisoquinoline-6-carboxamide A mixture of 176 mg of 2-(tetrahydrofuran-3-ylcarbonyl)-N-(tetrahydro-2H-pyran-2-yloxy)-1,2,3,4-tetrahydroisoquinoline-6-carboxamide, 6 ml methanol and 6 ml of an aqueous, 0.1 N hydrochloric acid is stirred overnight at ambient temperature. The reaction mixture is evaporated and the residue is dissolved in a mixture of water and acetonitrile and lyophilized. 140 mg of the title compound are obtained as colorless solid. MH+=291.2

14. N-Hydroxy-2-(pyridin-2-ylacetyl)-1,2,3,4-tetrahydroisoquinoline-6-carboxamide hydrochloride A mixture of 75 mg of 2-(pyridin-2-ylacetyl)-N-(tetrahydro-2H-pyran-2-yloxy)-1,2,3,4-tetrahydroisoquinoline-6-carboxamide, 6 ml methanol and 6 ml of an aqueous, 0.1 N hydrochloric acid is stirred overnight at ambient temperature. The reaction mixture is evaporated and the residue is dissolved in a mixture of 2 ml water and 2 ml acetonitrile and lyophilized. 75 mg of the title compound are obtained as colorless solid. MH+=312.1

15. N-Hydroxy-2-[(5-methoxy-1H-indol-2-yl)carbonyl]-1,2,3,4-tetrahydroisoquinoline-6-carboxamide A mixture of 45 mg of 2-[(5-methoxy-1H-indol-2-yl)carbonyl]-N-(tetrahydro-2H-pyran-2-yloxy)-1,2,3,4-tetrahydroisoquinoline-6-carboxamide, 3 ml isopropanol and 3 ml of an aqueous, 0.1 N hydrochloric acid is stirred overnight at ambient temperature. The reaction mixture is evaporated and the residue is treated with acetonitrile. The resulting solid is collected and dried. 25 mg of a colorless solid are obtained with mp 156° C. MH+=366.0

16. N-Hydroxy-2-(cyclopropylcarbonyl)-1,2,3,4-tetrahydroisoquinoline-6-carboxamide A mixture of 80 mg of 2-(cyclopropylcarbonyl)-N-(tetrahydro-2H-pyran-2-yloxy)-1,2,3,4-tetrahydroisoquinoline-6-carboxamide, 3 ml isopropanol and 3 ml of an aqueous, 0.1 N hydrochloric acid is stirred 4 h at ambient temperature. The reaction mixture is evaporated and the residue is dissolved in a mixture of 0.5 ml water and 0.5 ml acetonitrile and lyophilized. 90 mg of the title compound are obtained as solid with mp=90° C. MH+=261.1

17. 2-But-2-ynoyl-N-hydroxy-1,2,3,4-tetrahydroisoquinoline-7-carboxamide

A mixture of 124 mg 2-but-2-ynoyl-N-(tetrahydro-2H-pyran-2-yloxy)-1,2,3,4-tetrahydroisoquinoline-7-carboxamide, 6 ml methanol and 6 ml 0.1 N aqueous hydrochloric acid is stirred overnight at ambient temperature. The mixture is evaporated and the residue is treated with water and acetone. A colorless solid separates. After drying, 73 mg of the title compound are obtained. MH+=275.7

18. N-Hydroxy-2-(1H-indol-3-ylacetyl)-1,2,3,4-tetrahydroisoquinoline-7-carboxamide A mixture of 180 mg 2-(1H-indol-3-ylacetyl)-N-(tetrahydro-2H-pyran-2-yloxy)-1,2,3,4-tetrahydroisoquinoline-7-carboxamide, 6 ml methanol and 6 ml 0.1 N aqueous hydrochloric acid are stirred at ambient temperature overnight. The reaction mixture is evaporated and the residue is dissolved in a mixture of acetonitrile and water and lyophilized. 92 mg of the title compound are obtained. MH+=350.0

19. N-Hydroxy-2-(pyridin-3-ylacetyl)-1,2,3,4-tetrahydroisoquinoline-7-carboxamide hydrochloride A mixture of 140 mg 2-(pyridin-3-ylacetyl)-N-(tetrahydro-2H-pyran-2-yloxy)-1,2,3,4-tetrahydroisoquinoline-7-carboxamide in 6 ml methanol and 6 ml 0.1 N aqueous hydrochloric acid is stirred overnight at ambient temperature. Subsequently, the reaction mixture is evaporated. The residue is dissolved in a mixture of water and acetonitrile and lyophilized. 113 mg of the title compound are obtained as colorless solid. MH+=312.1

20. N-Hydroxy-2-(tetrahydrofuran-3-ylcarbonyl)-1,2,3,4-tetrahydroisoquinoline-7-carboxamide A mixture of 110 mg 2-(tetrahydrofuran-3-ylcarbonyl)-N-(tetrahydro-2H-pyran-2-yloxy)-1,2,3,4-tetrahydroisoquinoline-7-carboxamide in 6 ml methanol and 6 ml 0.1 N aqueous hydrochloric acid is stirred overnight at ambient temperature. Subsequently, the reaction mixture is evaporated. The residue is dissolved in a mixture of water and acetonitrile and lyophilized. The crude product is purified by silica gel flash chromatography. 20 mg of the title compound are obtained as colorless solid. MH+=291.1

21. N-Hydroxy-2-(pyridin-2-ylacetyl)-1,2,3,4-tetrahydroisoquinoline-7-carboxamide hydrochloride A mixture of 130 mg 2-(pyridin-2-ylacetyl)-N-(tetrahydro-2H-pyran-2-yloxy)-1,2,3,4-tetrahydroisoquinoline-7-carboxamide in 6 ml methanol and 6 ml 0.1 N aqueous hydrochloric acid is stirred overnight at ambient temperature. Subsequently, the reaction mixture is evaporated. The residue is dissolved in a mixture of water and acetonitrile and lyophilized. 105 mg of the title compound are obtained. MH+=312.1

22. N7-Hydroxy-N2-(2-phenylethyl)-3,4-dihydroisoquinoline-2,7(1H)-dicarboxamide A mixture of 200 mg N2-(2-phenylethyl)-N7-(tetrahydro-2H-pyran-2-yloxy)-3,4-dihydroisoquinoline-2,7(1H)-dicarboxamide in 6 ml methanol and 6 ml 0.1 N aqueous hydrochloric acid is stirred overnight at ambient temperature. Subsequently, the reaction mixture is evaporated. The residue is dissolved in a mixture of water and acetonitrile and lyophilized. The crude product is further purified by silica gel flash chromatography. 98 mg of the title compound are obtained. MH+=340.1

23. N-Hydroxy-2-(4-methylbenzoyl)-1,2,3,4-tetrahydroisoquinoline-7-carboxamide A mixture of 70 mg 2-(4-methylbenzoyl)-N-(tetrahydro-2H-pyran-2-yloxy)-1,2,3,4-tetrahydroisoquinoline-7-carboxamide in 6 ml methanol and 6 ml 0.1 N aqueous hydrochloric acid is stirred overnight at ambient temperature. Subsequently, the reaction mixture is evaporated. The residue is dissolved in a mixture of water and acetonitrile and lyophilized. The crude product is further purified by silica gel flash chromatography. 11 mg of the title compound are obtained as colorless solid. MH+=311.1

24. N-Hydroxy-2-[(5-methoxy-1H-indol-2-yl)carbonyl]-1,2,3,4-tetrahydroisoquinoline-7-carboxamide A mixture of 207 mg 2-[(5-methoxy-1H-indol-2-yl)carbonyl]-N-(tetrahydro-2H-pyran-2-yloxy)-1,2,3,4-tetrahydroisoquinoline-7-carboxamide in 6 ml methanol and 6 ml 0.1 N aqueous hydrochloric acid is stirred overnight at ambient temperature. Subsequently, the reaction mixture is evaporated. The residue is treated with 10 ml methanol at 60° C. for 1 h. The resulting solid is collected and dried. 43 mg of the title compound are obtained as colorless solid. MH+=365.0

25. 2-Acetyl-N-hydroxy-1,2,3,4-tetrahydroisoquinoline-7-carboxamide

To 6.29 g of 2-acetyl-N-(tetrahydro-2H-pyran-2-yloxy)-1,2,3,4-tetrahydroisoquinoline-7-carboxamide are added 57 ml water, 88 ml methanol and 1.4 g DowexWX2-100. The mixture is stirred overnight at ambient temperature and filtered.

The filtrate is evaporated and 4.17 g of the title compound as a yellow solid are obtained. MP 177-181° C.

26. Pyridin-3-ylmethyl 5-(hydroxycarbamoyl)-1,3-dihydro-2H-isoindole-2-carboxylate Solution 1:
Hydroxylamine hydrochloride (810 mg) are dissolved in dry methanol (11.5 mL) and a 2N solution of KOH in methanol (5.8 mL) is added. After 15 min the resulting solid is filtered and the filtrate is carefully evaporated to ca. 10 ml. 2-(Biphenyl-4-carbonyl)-2,3-dihydro-1H-isoindole-5-carboxylic acid methyl ester (360 mg) is suspended in THF (10 mL), solution 1 and a 2N solution of KOH in methanol (0.49 mL) is added and the reaction mixture is stirred for 4 h at ambient temperature. After evaporation, the crude product is purified by silica gel flash chromatography. 0.303 g of the title compound are obtained with MP 196-199° C.

27. N-Hydroxy-2-(quinolin-2-ylcarbonyl)isoindoline-5-carboxamide

Similar to example 26 the 0.20 g of the title compound are obtained with MP 162-166° C.

28. N-Hydroxy-2-(quinolin-6-ylcarbonyl)isoindoline-5-carboxamide

Similar to example 26 the 0.88 g of the title compound are obtained with MP 208-210° C.

29. N-Hydroxy-2-(isoquinolin-3-ylcarbonyl)isoindoline-5-carboxamide

Similar to example 26 0.228 g of the title compound are obtained with MP 208-210° C.

30. 2-(Biphenyl-4-ylcarbonyl)-N-hydroxyisoindoline-5-carboxamide

Solution 1:
Hydroxylamine hydrochloride (1.17 g) is dissolved in dry methanol (16.8 mL) and a 2N solution of KOH in methanol (8.4 mL) is added. After 15 min the resulting solid is filtered and the filtrate is carefully evaporated up to 10 ml. 2-(Biphenyl-4-carbonyl)-2,3-dihydro-1H-isoindole-5-carboxylic acid methyl ester (600 mg) is suspended in THF (10 mL) and solution 1 and 2N KOH in methanol (1.68 mL) is added. And the reaction mixture is stirred for 16 h at ambient temperature. After evaporation, the product is purified by silica gel flash chromatography. 0.37 g of the title compound is obtained with MP 160-190° C.

31. N-Hydroxy-2-(3-pyridin-3-ylpropanoyl)-1,2,3,4-tetrahydroisoquinoline-7-carboxamide hydrochloride The compound is prepared analogously to example 16 starting from 2-(3-pyridin-3-ylpropanoyl)-N-(tetrahydro-2H-pyran-2-yloxy)-1,2,3,4-tetrahydroisoquinoline-7-carboxamide. 125 mg of the title compound are obtained as yellowish lyophilisate with MH+=326.0

32. N7-Hydroxy-N2-(3-methoxypropyl)-3,4-dihydroisoquinoline-2,7(1H)-dicarboxamide The compound is prepared analogously to example 16 starting from N2-(3-methoxypropyl)-N7-(tetrahydro-2H-pyran-2-yloxy)-3,4-dihydroisoquinoline-2,7(1H)-dicarboxamide. 47 mg of the title compound are obtained as yellowish solid with MH+=308.0

33. 2-[4-(Dimethylamino)butanoyl]-N-hydroxy-1,2,3,4-tetrahydroisoquinoline-7-carboxamide hydrochloride The compound is prepared analogously to example 16 starting from 2-[4-(dimethylamino)butanoyl]-N-(tetrahydro-2H-pyran-2-yloxy)-1,2,3,4-tetrahydroisoquinoline-7-carboxamide. 145 mg of the title compound are obtained as reddish oil with MH+=305.9

34. 3-Methoxypropyl 7-(hydroxycarbamoyl)-3,4-dihydroisoquinoline-2(1H)-carboxylate The compound is prepared analogously to example 16 starting from 3-methoxypropyl 7-[(tetrahydro-2H-pyran-2-yloxy)carbamoyl]-3,4-dihydroisoquinoline-2(1H)-carboxylate. 85 mg of the title compound are obtained as nearly colorless solid with MH+=308.9

35. N7-Hydroxy-N2-methyl-3,4-dihydroisoquinoline-2,7(1H)-dicarboxamide

The compound is prepared analogously to example 16 starting from N2-methyl-N7-(tetrahydro-2H-pyran-2-yloxy)-3,4-dihydroisoquinoline-2,7(1H)-dicarboxamide. 90 mg of the title compound are obtained as yellowish lyophilisate with MH+=250.0

36. 2-(Cyclobutylcarbonyl)-N-hydroxy-1,2,3,4-tetrahydroisoquinoline-7-carboxamide The compound is prepared analogously to example 16 starting from 2-(cyclobutylcarbonyl)-N-(tetrahydro-2H-pyran-2-yloxy)-1,2,3,4-tetrahydroisoquinoline-7-carboxamide. 6 mg of the title compound are obtained as colorless solid with MH+=275.1

37. N-Hydroxy-2-(1H-indol-5-ylcarbonyl)-1,2,3,4-tetrahydroisoquinoline-7-carboxamide The compound is prepared analogously to example 16 starting from 2-(1H-indol-5-ylcarbonyl)-N-(tetrahydro-2H-pyran-2-yloxy)-1,2,3,4-tetrahydroisoquinoline-7-carboxamide. 90 mg of the title compound are obtained as colorless solid with MP=252° C. and MH+=336.0.

38. N-Hydroxy-2-[(2-methoxyethoxy)acetyl]-1,2,3,4-tetrahydroisoquinoline-7-carboxamide The compound is prepared analogously to example 16 starting from 2-[(2-methoxyethoxy)acetyl]-N-(tetrahydro-2H-pyran-2-yloxy)-1,2,3,4-tetrahydroisoquinoline-7-carboxamide. 84 mg of the title compound are obtained as colorless solid with MH+=309.0.

39. N-Hydroxy-2-[3-(2-methyl-1H-imidazol-1-yl)propanoyl]-1,2,3,4-tetrahydroisoquinoline-7-carboxamide hydrochloride The compound is prepared analogously to example 16 starting from 2-[3-(2-methyl-1H-imidazol-1-yl)propanoyl]-N-(tetrahydro-2H-pyran-2-yloxy)-1,2,3,4-tetrahydroisoquinoline-7-carboxamide. 238 mg of the title compound are obtained as yellowish solid with MP=63° C. and MH+=329.0.

40. Benzyl 6-(hydroxycarbamoyl)-3,4-dihydroisoquinoline-2(1H)-carboxylate

The compound is prepared analogously starting from benzyl 6-[(tetrahydro-2H-pyran-2-yloxy)carbamoyl]-3,4-dihydroisoquinoline-2(1H)-carboxylate. 113 mg of a colorless solid are obtained with MH+=327.1

41. N-Hydroxy-2-(phenoxyacetyl)-1,2,3,4-tetrahydroisoquinoline-6-carboxamide The compound is prepared analogously starting from 2-(phenoxyacetyl)-N-(tetrahydro-2H-pyran-2-yloxy)-1,2,3,4-tetrahydroisoquinoline-6-carboxamide. 95 mg of a nearly colorless solid are obtained with MH+=327.1.

42. N-Hydroxy-2-(4-methylbenzoyl)-1,2,3,4-tetrahydroisoquinoline-6-carboxamide The compound is prepared analogously starting from 2-(4-methylbenzoyl)-N-(tetrahydro-2H-pyran-2-yloxy)-1,2,3,4-tetrahydroisoquinoline-6-carboxamide. 40 mg of a colorless solid are obtained with MP=105-108° C.

43. N6-Hydroxy-N2-[2-(1H-indol-3-yl)ethyl]-3,4-dihydroisoquinoline-2,6(1H)-dicarboxamide The compound is prepared analogously starting from N2-[2-(1H-indol-3-yl)ethyl]-N6-(tetrahydro-2H-pyran-2-yloxy)-3,4-dihydroisoquinoline-2,6(1H)-dicarboxamide. 130 mg of a colorless solid are obtained with MP=173-176° C.

44. N6-Hydroxy-N2-benzyl-3,4-dihydroisoquinoline-2,6(1H)-dicarboxamide

The compound is prepared analogously starting from N2-benzyl-N6-(tetrahydro-2H-pyran-2-yloxy)-3,4-dihydroisoquinoline-2,6(1H)-dicarboxamide. 64 mg of a colorless solid are obtained with MP=149-153° C.

45. N6-Hydroxy-N2-(2-phenoxyethyl)-3,4-dihydroisoquinoline-2,6(1H)-dicarboxamide The compound is prepared analogously starting from N2-(2-phenoxyethyl)-N6-(tetrahydro-2H-pyran-2-yloxy)-3,4-dihydroisoquinoline-2,6(1H)-dicarboxamide. 150 mg of a colorless solid are obtained with MP=120-123° C.

46. N-hydroxy-2-(1H-Indol-5-ylcarbonyl)-1,2,3,4-tetrahydroisoquinoline-6-carboxamide The compound is prepared analogously starting from 2-(1H-Indol-5-ylcarbonyl)-N-(tetrahydro-2H-pyran-2-yloxy)-1,2,3,4-tetrahydroisoquinoline-6-carboxamide. The compound is purified by preparative HPLC.
Starting Materials

A1. 2-Benzyl 6-methyl 3,4-dihydroisoquinoline-2,6(1H)-dicarboxylate

A mixture of 10 g methyl 1,2,3,4-tetrahydroisoquinoline-6-carboxylate hydrochloride, 10 ml triethylamine, and 15 ml dichloromethane with 525 mg DMAP is stirred at 0° C. and 9.3 ml of benzyl chloroformate are added dropwise. After stirring overnight at ambient temperature, the reaction mixture is added to cold water. The organic phase is washed, dried, and evaporated. The crude product is purified by a silica gel chromatography.

A2. 2-[(Benzyloxy)carbonyl]-1,2,3,4-tetrahydroisoquinoline-6-carboxylic acid A mixture of 14.2 g 2-benzyl 6-methyl 3,4-dihydroisoquinoline-2,6(1H)-dicarboxylate, 50 ml THF and 32 ml of a 2M aqueous LiOH solution is stirred at ambient temperature overnight. The reaction mixture is added to 50 g of ice and the pH as adjusted to 2. The organic phase is separated, dried, and evaporated. 13.59 g of a colorless solid are obtained.

A3. Benzyl 6-[(tetrahydro-2H-pyran-2-yloxy)carbamoyl]-3,4-dihydroisoquinoline-2(1H)-carboxylate A mixture of 8.7 g 2-[(benzyloxy)carbonyl]-1,2,3,4-tetrahydroisoquinoline-6-carboxylic acid, 94 ml DMF, 35 ml triethylamine, 4.1 g HOBt and 17 g EDC is stirred for 30 min at ambient temperature. 3.3 g of tetrahydropyran-2-yl-hydroxylamine are added and the reaction mixture is stirred overnight. The mixture is added to a mixture of 100 ml water and 200 ml dichloromethane. The organic phase is separated, washed, dried and evaporated. The crude product is purified by silica gel flash chromatography. 11.08 g of the title compound are obtained as colorless oil.

A4. N-(Tetrahydro-2H-pyran-2-yloxy)-1,2,3,4-tetrahydroisoquinoline-6-carboxamide A mixture of 5 g benzyl 6-[(tetrahydro-2H-pyran-2-yloxy) carbamoyl]-3,4-dihydroisoquinoline-2(1H)-carboxylate, 250 mg Pd/C (5%), 250 ml ethanol and 5 ml triethylamine is hydrogenated at ambient hydrogen pressure. The reaction mixture is filtered, evaporated and 3.05 g of yellowish foam are obtained.

A5. 2-Tert-butyl-7-methyl-3,4-dihydroisoquinoline-2,7(1H)-dicarboxylate

A mixture of 25 g 2-(tert-butoxycarbonyl)-1,2,3,4-tetrahydroisoquinoline-7-carboxylic acid, 45.5 g of Boc2O, 650 mg DMAP, 7.5 ml methanol and 175 ml nitro methane is stirred at 50° C. over night. Additional 0.5 eq of Boc2O are added. After completion of the reaction, the mixture is diluted with ethyl acetate and washed with an aqueous solution of citric acid, sodium bicarbonate solution and water. After drying and evaporation of the organic phase, the crude product is purified by silica gel chromatography. 33.8 g of the title compound are obtained as yellowish oil.

A6. Methyl 1,2,3,4-tetrahydroisoquinoline-7-carboxylate

At 0° C. a mixture of 16.93 g 2-tert-butyl 7-methyl 3,4-dihydroisoquinoline-2,7(1H)-dicarboxylate, 160 ml dichloromethane and 80 ml trifluoroacetic acid is stirred for 30 min. Then, the mixture is stirred for 5 h at ambient temperature. The reaction mixture is evaporated and the residue is treated with a 10% KOH solution and dichloromethane. The organic layer is dried and evaporated. 22.18 g of the title compound are obtained.

The following intermediates are prepared similarly to the isomeric compounds described above.

A7. 2-Benzyl 7-methyl 3,4-dihydroisoquinoline-2,7(1H)-dicarboxylate

A8. 2-[(Benzyloxy)carbonyl]-1,2,3,4-tetrahydroisoquinoline-7-carboxylic acid

A9. Benzyl 7-[(tetrahydro-2H-pyran-2-yloxy)carbamoyl]-3,4-dihydroisoquinoline-2(1H)-carboxylate

A10. N-(Tetrahydro-2H-pyran-2-yloxy)-1,2,3,4-tetrahydroisoquinoline-7-carboxamide

A11. N-(Tetrahydro-2H-pyran-2-yloxy)isoindoline-5-carboxamide

A12. Benzyl 5-[(tetrahydro-2H-pyran-2-yloxy)carbamoyl]-1,3-dihydro-2H-isoindole-2-carboxylate

A13. 2-[(Benzyloxy)carbonyl]isoindoline-5-carboxylic acid

A14. 2-Benzyl 5-methyl 1,3-dihydro-2H-isoindole-2,5-dicarboxylate

A15. 3,4-Bis-bromomethyl-benzoic acid methyl ester 3,4-Dimethyl-benzoic acid methyl ester (10 g), N-bromosuccinimide (23.6 g) and AIBN (1.0 g) are heated in CCl4 (118 mL) 10 h at reflux temperature. After cooling and filtration, the mixture is evaporated and the residue is treated with CHCl$_3$ (ca. 200 mL) and an aqueous, saturated NaHCO$_3$-solution. After separation of the organic phase, drying and evaporation, the residue is crystallized from methanol. 8.7 g of the title compound are obtained with MP 74-75° C.

A16. 2-Benzyl-2,3-dihydro-1H-isoindole-5-carboxylic acid methyl ester 3,4-Bis-bromomethyl-benzoic acid methyl ester (20.0 g) benzylamine (6.7 g) and potassium carbonate are mixtured with THF (30 mL) and MeOH (150 mL) and the reaction mixture is stirred overnight. After filtration and evaporation, the residue is treated with MTBE and water. The organic phase is separated and dried. The crude product is purified by silica gel flash chromatography. 9.1 g of the title compound are obtained.

A17. 1,3-Dihydro-isoindole-2,5-dicarboxylic acid 2-benzyl ester 5-methyl ester 2-Benzyl-2,3-dihydro-1H-isoindole-5-carboxylic acid methyl ester (3.9 g) and NaHCO$_3$ (12.3 g) are suspended in CH$_2$Cl$_2$ (50 mL) and the mixture is treated with benzylchloroformate (Z—Cl) (10.8 mL). The mixture is warmed to 30° C. and after 10 min the reaction mixture is added to a mixture of water (150 mL) with NaHCO$_3$ (12.3 g), the organic phase is separated, dried and evaporated. To the residue are added MeOH and the crystalline solid is collected and dried. 3.79 g of the title compound are obtained with MP 59-65° C.

A18. 1,3-Dihydro-isoindole-2,5-dicarboxylic acid 2-benzyl ester 1,3-Dihydro-isoindole-2,5-dicarboxylic acid 2-benzyl ester 5-methyl ester (2.25 g) is suspended in THF (8 mL) and treated with an aqueous 2N LiOH solution. (5.51 mL) and stirred 14 h at ambient temperature. After evaporation, the residue is partitioned between dichloromethane and water. The organic phase is dried and evaporated. 2.05 g of the title compound are obtained with MP 197-199° C.

A19. 2-(Toluene-4-sulfonyl)-2,3-dihydro-1H-isoindole-5-carboxylic acid methyl ester Sodium (0.60 g) is dissolved in methanol (100 mL) and toluene sulfonamide (4.25 g) is added portion wise. After 30 min at ambient temperature 3,4-bis-bromomethyl-benzoic acid methyl ester are added (4.00 g). After stirring overnight, the resulting solid is collected, washed with methanol and dried. 2.80 g of the title compound are obtained with MP=164-166° C.

A20. 2,3-Dihydro-1H-isoindole-5-carboxylic acid methyl ester compound with hydrobromic acid 2-(Toluene-4-sulfonyl)-2,3-dihydro-1H-isoindole-5-carboxylic acid methyl ester (5.00 g) are dissolved in 33% HBr/HOAc (39 mL) and stirred for 16 h at ambient temperature. The reaction mixture is evaporated and the residue is treated with MeOH (40 mL). The resulting solid is separated, washed and dried. 3.00 g of the title compound are obtained with MP of 243-246° C.

A21. 2-(Biphenyl-4-carbonyl)-2,3-dihydro-1H-isoindole-5-carboxylic acid methyl ester 2,3-Dihydro-1H-isoindole-5-carboxylic acid methyl ester compound with hydrobromic acid (0.80 g), triethylamine (1.30 mL) and biphenyl-4-carbonyl chloride (0.67 g) are stirred in THF (35 mL) at ambient temperature. After 1.5 h the mixture is treated with CHCl$_3$ washed, dried and evaporated until a solid starts to separate. The product is fully crystallized by adding heptane. 0.94 g of the title compound is obtained with MP 172-180° C.

In a similar way are prepared:

A22. 1,3-Dihydro-isoindole-2,5-dicarboxylic acid 5-methyl ester 2-pyridin-3-ylmethyl ester

A23. 2-(Quinoline-2-carbonyl)-2,3-dihydro-1H-isoindole-5-carboxylic acid methyl ester

A24. 2-(Quinoline-6-carbonyl)-2,3-dihydro-1H-isoindole-5-carboxylic acid methyl ester

A25. 2-(isoquinoline-3-carbonyl)-2,3-dihydro-1H-isoindole-5-carboxylic acid methyl ester

A26. 2-(1H-Indol-3-ylacetyl)-N-(tetrahydro-2H-pyran-2-yloxy)-1,2,3,4-tetrahydroisoquinoline-6-carboxamide 200 mg of N-(tetrahydro-2H-pyran-2-yloxy)-1,2,3,4-tetrahydroisoquinoline-6-carboxamide, 140 mg Indolyl-3-acetic acid, 98 mg HOBT and 0.6 ml Et3N are dissolved in 8 ml DMF. To this mixture are added 278 mg EDC and the mixture is stirred overnight. The reaction mixture is evaporated and the crude product is purified by silica gel flash chromatography. 180 mg of the title compound are obtained in 57% yield.

A27. 2-(Pyridin-2-ylacetyl)-N-(tetrahydro-2H-pyran-2-yloxy)-1,2,3,4-tetrahydroisoquinoline-6-carboxamide 200 mg of N-(tetrahydro-2H-pyran-2-yloxy)-1,2,3,4-tetrahydroisoquinoline-6-carboxamide, 69 mg of 2-pyridineacetic acid, 111 mg HOBT, 276 mg EDC and 0.6 ml triethylamine are dissolved in 7 ml DMF and stirred overnight. The mixture is evaporated and the residue is treated with 5 ml water and 10 ml of dichloromethane. After separation, the water phase is washed with dichloromethane and the combined organic phases are filtered, dried and evaporated. 80 mg of a colorless oil are obtained.

A28. 2-(Cyclobutylcarbonyl)-N-(tetrahydro-2H-pyran-2-yloxy)-1,2,3,4-tetrahydroisoquinoline-6-carboxamide 200 mg of N-(tetrahydro-2H-pyran-2-yloxy)-1,2,3,4-tetrahydroisoquinoline-6-carboxamide, 80 mg of cyclobutan carboxylic acid, 111 mg HOBT, 276 mg EDC and 0.6 ml triethylamine are dissolved in 7 ml DMF and stirred overnight. The mixture is evaporated and the residue is purified by silica gel chromatography. 170 mg of a yellowish foam are obtained.

A29. N2-(3-Methoxypropyl)-N6-(tetrahydro-2H-pyran-2-yloxy)-3,4-dihydroisoquinoline-2,6(1H)-dicarboxamide A mixture of 0.074 ml 3-methoxyproylamine in 4 ml DMF is treated under an inert gas atmosphere is treated with 117 mg carbonyldiimidazole. After 2 h at ambient temperature the resulting mixture is treated with 200 mg of N-(tetrahydro-2H-pyran-2-yloxy)-1,2,3,4-tetrahydroisoquinoline-6-carboxamide and 10 mg DMAP. The reaction mixture is stirred overnight. After addition of 2 ml water the mixture is extracted twice with dichloromethane and the combined organic phases are dried and evaporated. The residue is purified by silica gel flash chromatography. 180 mg of yellowish oil are obtained.

A30. 3-Methoxypropyl-6-[(tetrahydro-2H-pyran-2-yloxy)carbamoyl]-3,4-dihydroisoquinoline-2(1H)-carboxylate A solution of 0.069 ml 3-methoxypropanol in 4 ml dichloromethane are treated with 117 mg carbonyldiimidazole and 10 mg p-toluenesulfonic acid. After 2 h at ambient temperature, 200 mg of N-(tetrahydro-2H-pyran-2-yloxy)-1,2,3,4-tetrahydroisoquinoline-6-carboxamide are added and the reaction mixture is stirred overnight at ambient temperature. Subsequently, the mixture is treated with 2 ml of water and the organic phase is separated. The aqueous phase is extracted twice with 5 ml dichloromethane, dried and evaporated. 100 mg of colorless oil are obtained.

A31. 2-(3-Pyridin-3-ylpropanoyl)-N-(tetrahydro-2H-pyran-2-yloxy)-1,2,3,4-tetrahydroisoquinoline-6-carboxamide A mixture of 200 mg N-(tetrahydro-2H-pyran-2-yloxy)-1,2,3,4-tetrahydroisoquinoline-6-carboxamide, 120 mg of 3-(3-pyridyl)propionic acid, 111 mg HOBt, 276 mg EDC, 0.603 ml triethylamine and 7 ml DMF is stirred overnight. The resulting reaction mixture is purified by silica gel chromatography. 154 mg of the title compound are obtained as colorless foam.

A32. 2-(3-Pyridin-3-ylpropanoyl)-N-(tetrahydro-2H-pyran-2-yloxy)-1,2,3,4-tetrahydroisoquinoline-6-carboxamide A mixture of 200 mg N-(tetrahydro-2H-pyran-2-yloxy)-1,2,3,4-tetrahydroisoquinoline-6-carboxamide, 109 mg 3-pyridylacetic acid, 111 mg HOBt, 276 mg EDC, 0.603 ml triethylamine and 7 ml DMF is stirred overnight. The reaction mixture is purified by silica gel chromatography. 55 mg of the title compound are obtained as nearly colorless foam.

A33. 2-[4-(Dimethylamino)butanoyl]-N-(tetrahydro-2H-pyran-2-yloxy)-1,2,3,4-tetrahydroisoquinoline-6-carboxamide A mixture of 200 mg N-(tetrahydro-2H-pyran-2-yloxy)-1,2,3,4-tetrahydroisoquinoline-6-carboxamide, 67 mg 4-dimethylaminobutyric acid hydrochloride, 111 mg HOBt, 276 mg EDC, 0.603 ml triethylamine and 7 ml DMF is stirred overnight. The reaction mixture is quenched with 3 ml water and 5 ml dichloromethane. The organic phase is separated, the water phase extracted twice with dichloromethane. The combined organic phases are dried and evaporated. 280 ml of a yellow oil is obtained, which is further purified by preparative HPLC-methods.

A34. 2-[(2-Methyl-1H-imidazol-1-yl)acetyl]-N-(tetrahydro-2H-pyran-2-yloxy)-1,2,3,4-tetrahydroisoquinoline-6-carboxamide A mixture of 200 mg N-(tetrahydro-2H-pyran-2-yloxy)-1,2,3,4-tetrahydroisoquinoline-6-carboxamide, 61 mg 3-(2-methyl-1H-imidazol-1-yl)propan acid, 111 mg HOBt, 276 mg EDC, 0.603 ml triethylamine and 7 ml DMF is stirred overnight. The reaction mixture is quenched with 3 ml water and 5 ml dichloromethane. The organic phase is separated, the water phase extracted with dichloromethane. The combined organic phases are dried and evaporated. 315 ml of yellow oil is obtained, which is further purified by preparative HPLC-methods.

A35. 2-[(2-Methoxyethoxy)acetyl]-N-(tetrahydro-2H-pyran-2-yloxy)-1,2,3,4-tetrahydroisoquinoline-6-carboxamide A mixture of 200 mg N-(tetrahydro-2H-pyran-2-yloxy)-1,2,3,4-tetrahydroisoquinoline-6-carboxamide, 0.045 ml 2-(2-methoxyethoxy)acetic acid, 111 mg HOBt, 276 mg EDC, 0.603 ml triethylamine and 7 ml DMF is stirred overnight. The reaction mixture is quenched with 3 ml water and 5 ml dichloromethane. The organic phase is separated, the water phase extracted with 2 ml dichloromethane. The combined organic phases are dried and evaporated. 335 ml of yellow oil is obtained, which is further purified by preparative HPLC-methods.

A36. 2-Acetyl-N-(tetrahydro-2H-pyran-2-yloxy)-1,2,3,4-tetrahydroisoquinoline-6-carboxamide A mixture of 200 mg N-(tetrahydro-2H-pyran-2-yloxy)-1,2,3,4-tetrahydroisoquinoline-6-carboxamide, 0.046 m acetic acid, 111 mg HOBt, 276 mg EDC, 0.603 ml triethylamine and 7 ml DMF is stirred 4 h at ambient temperature. The reaction mixture is then purified by silica gel chromatography.

A37. 2-(Tetrahydrofuran-3-ylcarbonyl)-N-(tetrahydro-2H-pyran-2-yloxy)-1,2,3,4-tetrahydroisoquinoline-6-carboxamide A mixture of 200 mg N-(tetrahydro-2H-pyran-2-yloxy)-1,2,3,4-tetrahydroisoquinoline-6-carboxamide, 0.038 ml tetrahydrofuryl-3-carboxylic acid, 111 mg HOBt, 276 mg EDC, 0.603 ml triethylamine and 7 ml DMF is stirred overnight at ambient temperature. The reaction mixture is added to a mixture of 20 ml water and 50 ml dichloromethane. The water phase is washed twice with dichloromethane and the combined organic phases are dried and evaporated. The residue is then purified by silica gel chromatography. 176 mg of the title compound are obtained as colorless foam after drying.

A38. 2-(Pyridin-2-ylacetyl)-N-(tetrahydro-2H-pyran-2-yloxy)-1,2,3,4-tetrahydroisoquinoline-6-carboxamide A mixture of 200 mg N-(tetrahydro-2H-pyran-2-yloxy)-1,2,3,4-tetrahydroisoquinoline-6-carboxamide, 69 mg 2-pyridyl-acetic acid, 111 mg HOBt, 276 mg EDC, 0.603 ml triethylamine and 7 ml DMF is stirred overnight at ambient temperature. The reaction mixture is added to a mixture of 5 ml water and 10 ml dichloromethane. The water phase is washed with dichloromethane and the combined organic phases are dried and evaporated. 80 mg of the title compound are obtained as colorless oil.

A39. 2-[(5-Methoxy-1H-indol-2-yl)carbonyl]-N-(tetrahydro-2H-pyran-2-yloxy)-1,2,3,4-tetrahydroisoquinoline-6-carboxamide A mixture of 200 mg N-(tetrahydro-2H-pyran-2-yloxy)-1,2,3,4-tetrahydroisoquinoline-6-carboxamide, 152 mg 5-methoxyindol-2-carboxylic acid, 111 mg HOBt, 276 mg EDC, 0.603 ml triethylamine and 7 ml DMF is stirred overnight at ambient temperature. The reaction mixture is evaporated. The residue is then purified by silica gel chromatography. 50 mg of the title compound are obtained as yellowish foam.

A40. 2-(Cyclopropylcarbonyl)-N-(tetrahydro-2H-pyran-2-yloxy)-1,2,3,4-tetrahydroisoquinoline-6-carboxamide A mixture of 200 mg N-(tetrahydro-2H-pyran-2-yloxy)-1,2,3,4-tetrahydroisoquinoline-6-carboxamide, 0.063 ml cyclopropylcarboxylic acid, 111 mg HOBt, 276 mg EDC, 0.603 ml triethylamine and 7 ml DMF is stirred overnight at ambient temperature. The reaction mixture is evaporated. The residue is then purified by silica gel chromatography. 91 mg of the title compound are obtained.

A41. 2-But-2-ynoyl-N-(tetrahydro-2H-pyran-2-yloxy)-1,2,3,4-tetrahydroisoquinoline-7-carboxamide A mixture of 200 mg N-(tetrahydro-2H-pyran-2-yloxy)-1,2,3,4-tetrahydroisoquinoline-7-carboxamide, 67 mg butynoic acid, 98 mg HOBt, 278 mg EDC, 0.6 ml triethylamine and 8 ml DMF is stirred overnight at ambient temperature. The mixture is evaporated and the residue is purified by silica gel flash chromatography. 130 mg of a colorless foam are obtained after drying.

A42. 2-(1H-Indol-3-ylacetyl)-N-(tetrahydro-2H-pyran-2-yloxy)-1,2,3,4-tetrahydroisoquinoline-7-carboxamide A mixture of 200 mg N-(tetrahydro-2H-pyran-2-yloxy)-1,2,3,4-tetrahydroisoquinoline-7-carboxamide, 140 mg indole-3-acetic acid, 98 mg HOBt, 278 mg EDC, 0.6 ml triethylamine and 8 ml DMF is stirred overnight at ambient temperature. The mixture is evaporated. 910 mg of a residue are obtained. The residue is purified by silica gel flash chromatography. 180 mg of the title compound are obtained after drying.

A43. 2-(Pyridin-3-ylacetyl)-N-(tetrahydro-2H-pyran-2-yloxy)-1,2,3,4-tetrahydroisoquinoline-7-carboxamide A mixture of 200 mg N-(tetrahydro-2H-pyran-2-yloxy)-1,2,3,4-tetrahydroisoquinoline-7-carboxamide, 109 mg 3-pyridylacetic acid, 98 mg HOBt, 278 mg EDC, 0.6 ml triethylamine and 8 ml DMF is stirred overnight at ambient temperature. The mixture is evaporated. The residue is purified by silica gel flash chromatography. 146 mg of the title compound are obtained after drying as colorless foam.

A44. 2-(Tetrahydrofuran-3-ylcarbonyl)-N-(tetrahydro-2H-pyran-2-yloxy)-1,2,3,4-tetrahydroisoquinoline-7-carboxamide A mixture of 200 mg N-(tetrahydro-2H-pyran-2-yloxy)-1,2,3,4-tetrahydroisoquinoline-7-carboxamide, 92 mg 3-tetrahydrofuranecarboxylic acid, 98 mg HOBt, 278 mg EDC, 0.6 ml triethylamine and 8 ml DMF is stirred overnight at ambient temperature. The mixture is evaporated. 1.09 g of the residue are purified by silica gel flash chromatography. 110 mg of the title compound are obtained after drying as colorless foam.

A45. 2-(Pyridin-2-ylacetyl)-N-(tetrahydro-2H-pyran-2-yloxy)-1,2,3,4-tetrahydroisoquinoline-7-carboxamide A mixture of 200 mg N-(tetrahydro-2H-pyran-2-yloxy)-1,2,3,4-tetrahydroisoquinoline-7-carboxamide, 138 mg 2-pyridylacetic acid, 98 mg HOBt, 278 mg EDC, 0.6 ml triethylamine and 8 ml DMF is stirred overnight at ambient temperature. The mixture is evaporated. 0.98 g of the residue are purified by silica gel flash chromatography. 130 mg of the title compound are obtained after drying as colorless foam.

A46. N2-(2-Phenylethyl)-N7-(tetrahydro-2H-pyran-2-yloxy)-3,4-dihydroisoquinoline-2,7(1H)-dicarboxamide A mixture of 200 mg N-(tetrahydro-2H-pyran-2-yloxy)-1,2,3,4-tetrahydroisoquinoline-7-carboxamide, 117 mg phenylethyl-isocyanat, 98 mg HOBt, 278 mg EDC, 0.6 ml triethylamine and 8 ml DMF is stirred overnight at ambient temperature. The mixture is evaporated. The residue is purified by silica gel flash chromatography. 208 mg of the title compound are obtained after drying as colorless foam.

A47. 2-(4-Methylbenzoyl)-N-(tetrahydro-2H-pyran-2-yloxy)-1,2,3,4-tetrahydroisoquinoline-7-carboxamide A mixture of 200 mg N-(tetrahydro-2H-pyran-2-yloxy)-1,2,3,4-tetrahydroisoquinoline-7-carboxamide, 108 mg 4-methylbenzoic acid, 98 mg HOBt, 278 mg EDC, 0.6 ml triethylamine and 8 ml DMF is stirred overnight at ambient temperature. The mixture is evaporated. The residue is purified by silica gel flash chromatography. 77 mg of the title compound are obtained after drying as colorless foam.

A48. 2-[(5-Methoxy-1H-indol-2-yl)carbonyl]-N-(tetrahydro-2H-pyran-2-yloxy)-1,2,3,4-tetrahydroisoquinoline-7-carboxamide A mixture of 200 mg N-(tetrahydro-2H-pyran-2-yloxy)-1,2,3,4-tetrahydroisoquinoline-7-carboxamide, 152 mg 5-methoxyindolyl-2-carboxylic acid, 98 mg HOBt, 278 mg EDC, 0.6 ml triethylamine and 8 ml DMF is stirred overnight at ambient temperature. The mixture is evaporated. The residue is purified by silica gel flash chromatography. 212 mg of the title compound are obtained after drying as colorless foam.

A49. 2-Acetyl-N-(tetrahydro-2N-pyran-2-yloxy)-1,2,3,4-tetrahydroisoquinoline-7-carboxamide 12.1 g of 2-acetyl-1,2,3,4-tetrahydroisoquinoline-7-carboxylic acid are dissolved in 183 ml DMF, 8.14 g HOBt and 6.42 g O-(tetrahydropyran-2-yl)-hydroxylamine are added and the mixture is stirred at ambient temperature for 1 h. The mixture is cooled to 0° C. and to the mixture are added 21.09 g EDC and it is stirred overnight. The mixture is diluted with water and dichloromethane is added. The combined organic phases are dried and evaporated. The residue is purified by means of a silica gel chromatography. 7.25 g of colorless oil are obtained.

In a similar way are prepared:

A50. 2-(3-Pyridin-3-ylpropanoyl)-N-(tetrahydro-2H-pyran-2-yloxy)-1,2,3,4-tetrahydroisoquinoline-7-carboxamide

A51. N2-(3-Methoxypropyl)-N7-(tetrahydro-2H-pyran-2-yloxy)-3,4-dihydroisoquinoline-2,7(1H)-dicarboxamide

A52. 2-[4-(Dimethylamino)butanoyl]-N-(tetrahydro-2H-pyran-2-yloxy)-1,2,3,4-tetrahydroisoquinoline-7-carboxamide

A53. 3-Methoxypropyl-7-[(tetrahydro-2H-pyran-2-yloxy)carbamoyl]-3,4-dihydroisoquinoline-2(1H)-carboxylate

A54. N2-Methyl-N7-(tetrahydro-2H-pyran-2-yloxy)-3,4-dihydroisoquinoline-2,7(1H)-dicarboxamide

A55. 2-(Cyclobutylcarbonyl)-N-(tetrahydro-2H-pyran-2-yloxy)-1,2,3,4-tetrahydroisoquinoline-7-carboxamide

A56. 2-[(2-Methoxyethoxy)acetyl]-N-(tetrahydro-2H-pyran-2-yloxy)-1,2,3,4-tetrahydroisoquinoline-7-carboxamide

A57. 2-[(3-(2-Methyl-1H-imidazol-1-yl)propanoyl]-N-(tetrahydro-2H-pyran-2-yloxy)-1,2,3,4-tetrahydroisoquinoline-7-carboxamide

A58. 2-(Phenoxyacetyl)-N-(tetrahydro-2H-pyran-2-yloxy)-1,2,3,4-tetrahydroisoquinoline-6-carboxamide

A59. 2-(4-Methylbenzoyl)-N-(tetrahydro-2H-pyran-2-yloxy)-1,2,3,4-tetrahydroisoquinoline-6-carboxamide

A60. N2-[2-(1H-Indol-3-yl)ethyl]-N6-(tetrahydro-2H-pyran-2-yloxy)-3,4-dihydroisoquinoline-2,6(1H)-dicarboxamide

A61. N2-Benzyl-N6-(tetrahydro-2H-pyran-2-yloxy)-3,4-dihydroisoquinoline-2,6(1H)-dicarboxamide

A62. N2-(2-Phenoxyethyl)-N6-(tetrahydro-2H-pyran-2-yloxy)-3,4-dihydroisoquinoline-2,6(1H)-dicarboxamide

A63. 2-(1H-Indol-5-ylcarbonyl)-N-(tetrahydro-2H-pyran-2-yloxy)-1,2,3,4-tetrahydroisoquinoline-6-carboxamide

A64. N2-Methyl-N6-(tetrahydro-2H-pyran-2-yloxy)-3,4-dihydroisoquinoline-2,6(1H)-dicarboxamide

A65. 2-Acetyl-1,2,3,4-tetrahydro-isoquinoline-7-carboxylic acid 30.6 g 1,2,3,4-tetrahydro-7-isoquinolinecarboxylic acid are dissolved in 383 ml THF 109 ml acetic acid anhydride are added and the mixture is stirred for 5 h at ambient temperature. The resulting solid is collected and dried. 12.1 g of a colorless solid are obtained.

Commercial Utility

The compounds according to this invention have valuable pharmacological properties and effects, which make them commercially applicable, such as e.g. they are commercially utilizable by properties related to inhibiting histone deacetylase activity and function, in particular HDAC6 activity and function.

"Histone deacetylase" (HDAC) means an enzyme with an activity towards the ε-acetyl group of lysine residues within a substrate protein. In particular histone deacetylases catalyse the hydrolysis the ε-acetyl group of lysine residues within these substrate proteins, forming the free amino group of lysine.

Inhibition of histone deacetylase by compounds according to this invention means inhibiting the activity and function of one or more HDAC isoenzymes, in particular isoenzymes selected from the so far known histone deacetylases, namely HDAC 1, 2, 3 and 8 (class I) and HDAC 4, 5, 6, 7, 10 (class II), HDAC 11 as well as the NAD+ dependent class III (Sir2 homologues). In some preferred embodiment this inhibition is at least about 50%, more preferable at least 75% and still more preferable above 90%. Most preferable, this inhibition is specific to HDAC6 as a selected class II enzyme. In a preferred embodiment, the selectivity is greater than 10 fold, more preferable greater than 50 fold and most preferable greater than 100 fold, as compared to the class I enzyme HDAC1. A histone deacetylase inhibitor in the meaning of this invention is therefore a compound capable of interacting with a histone deacetylase and inhibiting its activity, in particular its enzymatic activity. A HDAC6 selective inhibitor in the meaning of this invention is therefore a compound interacting with HDAC6 thereby inhibiting its activity, in particular its enzymatic activity, with a higher potency relative to HDAC1 as a representative for a HDAC class I enzyme. In this context "head group" defines the residues within a histone deacetylase inhibitor responsible for interacting with the active site of the enzyme, e.g. the $Zn^{2+}$ ion.

The inhibition of histone deacetylases is determined in biochemical assays of various formats and sources of enzymatic activity. HDAC activity is used either derived from nuclear or cellular extracts or by heterologous expression of defined HDAC isoenzymes in E. coli, insect cells or mammalian cells. Since HDACs are active in multiprotein complexes and form homo- and heterodimers, nuclear extracts derived from human cancer cells, for example the human cervical carcinoma cell line HeLa, are preferred. These nuclear extracts contain class I and class II enzymes, but are enriched in class I enzymes. For expression of recombinant HDAC 1 and HDAC6 isoenzymes, mammalian expression systems like HEK293 cells are preferred. The HDAC isoenzyme is expressed as a fusion protein with an affinity tag, like the FLAG epitope. By affinity chromatography, the tagged protein is purified alone or in complex with endogenous proteins (e.g. other HDAC isoenzmyes and coactivators/platform proteins). The biochemical assays are well described and well known to persons skilled in the art. As substrates, histone proteins, peptides derived from histone proteins or other HDAC substrates as well as acetylated lysine mimetics are used. One preferred promiscuous HDAC substrate is the tripeptide Ac-NH-GGK(Ac), coupled with the fluorophore 7-aminomethylcoumarin (AMC).

The invention further relates to the use of the compounds according to this invention for inhibiting histone deacetylase activity, in particular HDAC6 activity, in cells and tissues, causing hyperacetylation of respective substrate proteins like α-tubulin or Hsp90 and as functional consequence, for example, inhibition of cell migration and/or proliferation, inhibition of chaperone function and protein folding as well as interference with protein degradation, cell cycle arrest and/or induction of apoptosis.

The cellular activity of a histone deacetylase inhibitor, in particular a HDAC6 selective inhibitor, includes any cellular effect related to histone deacetylase inhibition, in particular protein hyperacetylation, chemosensitization, inhibition of cell migration and/or proliferation and induction of apoptosis.

The term "induction of apoptosis" and analogous terms are used to identify a compound which executes programmed cell death in cells contacted with that compound. "Apoptosis" is defined by complex biochemical events within the contacted cell, such as the activation of cysteine specific proteinases ("caspases") and the fragmentation of chromatin. Induction of apoptosis in cells contacted with the compound might not necessarily coupled with inhibition of cell proliferation or cell differentiation. Preferably, the inhibition of proliferation, induction of differentiation and/or induction of apoptosis is specific to cells with aberrant cell growth.

The term "chemosensitization" is understood in a broad sense as sensitizing neoplastic cells for anti-proliferative and/or pro-apoptotic stimuli in general ("synergistic activity"). These stimuli include, for example, agents interfering with the function of the mitotic spindle like taxanes or epothilones as tubulin stabilizing agents or anti-hormonal therapies including anti-estrogens, but also cytotoxic and targeted cancer agents in general used in experimental or clinical cancer therapy and finally radiation therapy.

Assays for quantification of cell proliferation or apoptosis are well known to experts and state of the art. For example, metabolic activity which is linked to cellular proliferation is quantified using the Alamar Blue/Resazurin assay (O'Brian et al. Eur J Biochem 267, 5421-5426, 2000) and induction of apoptosis is quantified by measurement of chromatin fragmentation with the cell death detection ELISA commercialized by Roche. Examples for cellular assays to determine hyperacetylation of HDAC substrates are given by measuring core histone, α-tubulin or Hsp90 hyperacetylation using specific antibodies by Western blotting. In-vitro assays for measuring cell migration are also well known to experts and state of the art. These include scratch assays followed by microscopic analysis as well as the transwell migration assay as described (Sap et al. Oncogene published on-line Apr. 4, 2005).

Compounds according to this invention can be commercially applicable due to their HDAC, in particular HDAC6 inhibitory activity, anti-proliferative and/or apoptosis inducing activity and/or chemosensitization and/or inhibition of cell migration which may be beneficial in the therapy or prophylaxis of diseases responsive thereto, such as e.g. any of those diseases mentioned herein.

The invention further relates to a method for inhibiting, treating, ameliorating or preventing cellular malignant or non-malignant neoplasia by administration of an effective amount of a compound according to this invention to a mammal, in particular a human in need of such treatment. A "neoplasia" is defined by cells displaying aberrant cell proliferation and/or survival and/or a block in differentiation. The term neoplasia includes "benign neoplasia" which is described by hyperproliferation of cells, incapable of forming an aggressive, metastasizing tumor in-vivo, and, in contrast, "malignant neoplasia" which is described by cells with multiple cellular and biochemical abnormalities, capable of forming a systemic disease, for example forming tumor metastasis in distant organs.

The compounds according to the present invention are preferably used for the treatment of malignant neoplasia, also described as cancer, characterized by tumor cells finally metastasizing into distinct organs or tissues. Examples of malignant neoplasia treated with the compounds of the present invention include solid and hematological tumors. Solid tumors are exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasia includes inherited cancers exemplified by Retinoblastoma and Wilms tumor. In addition, malignant neoplasia includes primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkin's disease, multiple myeloma and T-cell lymphoma. Also included are myelodysplastic syndromes such as Polycythemia vera, Essential thrombocytosis or Myelofibrosis, plasma cell neoplasia, paraneoplastic syndromes, and cancers of unknown primary site as well as AIDS related malignancies. Also included are precancerous skin growth diseases such as actinic keratosis.

Neoplastic cell proliferation might also affect normal cell behaviour and organ function. For example the formation of new blood vessels, a process described as neovascularization, is induced by tumors or tumor metastases. Compounds according to this invention can be commercially applicable for treatment of pathophysiological relevant processes caused by benign or neoplastic cell proliferation, such as but not limited to neovascularization.

Drug resistance is of particular importance for the frequent failure of standard cancer therapeutics. This drug resistance is caused by various cellular and molecular mechanisms like overexpression of drug efflux pumps, mutation within the cellular target protein or loss of target protein expression. The commercial applicability of compounds according to the present invention is not limited to $1^{st}$ line treatment of patients. Patients with resistance to cancer chemotherapeutics or target specific anti-cancer drugs can be also amenable for treatment with these compounds for e.g. $2^{nd}$ or $3^{rd}$ line treatment cycles. A prominent example is given by breast cancer patients without expression of the estrogen receptor and resistant to standard anti-hormonal therapy with e.g. Tamoxifen. The compounds according to the present invention might also be used in combination with standard chemotherapeutic or targeted drugs to resensitize tumors towards these agents or to synergize with these agents.

In the context of their properties, functions and usabilities mentioned herein, the compounds according to the present invention are expected to be distinguished by valuable and desirable effects related therewith, such as e.g. by low toxicity, superior bioavailability in general (such as e.g. good enteral absorption), superior therapeutic window, absence of significant side effects, and/or further beneficial effects related with their therapeutic and pharmaceutical suitability.

The invention further provides a method for treating a mammal, in particular a human, bearing a hyperproliferative disease different to cellular neoplasia, sensitive to histone deacetylase inhibitor therapy comprising administering to said mammal a pharmacologically active and therapeutically effective and tolerable amount of a compound according to this invention. These non-malignant diseases include:

(i) arthropathies and osteopathological conditions or diseases such as rheumatoid arthritis, osteoarthritis, gout, polyarthritis, and psoriatic arthritis;

(ii) autoimmune diseases like systemic lupus erythematosus and transplant rejection;

(iii) hyperproliferative diseases such as smooth muscle cell proliferation including vascular proliferative disorders, atherosclerosis, restenosis;

(iv) fibro-proliferative diseases such as lung fibrosis, systemic sclerosis and scleroderma, retroperitoneal fibrosis, nephrogenic systemic fibrosis, renal fibrosis, hepatic fibrosis, cardiac fibrosis, chronic kidney disease and polycystic kidney disease;

(v) acute and chronic inflammatory conditions or diseases and dermal conditions such as psoriasis, ulcerative colitis, Crohn's disease, chronic pancreatitis, hepatitis, liver cirrhosis, allergic rhinitis, allergic dermatitis, cystic fibrosis, chronic obstructive bronchitis, chronic obstructive pulmonary disease (COPD) and asthma;

(vi) endometriosis, uterine fibroids, endometrial hyperplasia, fatty liver disease, non-alcoholic steato-hepatitis and benign prostate hyperplasia;

(vii) cardiac dysfunction such as diastolic heart failure;

(viii) inhibiting immunosuppressive conditions like HIV infections;

(ix) neuropathological disorders like Multiple Sclerosis, Parkinsons disease, Alzheimers disease, Huntingtons disease or polyglutamine related disorders;

(x) pathological conditions amenable to treatment by potentiating of endogenous gene expression as well as enhancing transgene expression in gene therapy;

(xi) muscle dystrophy with Duchenne's muscular dystrophy as one example;

(xii) various forms of diabetes, including insulin resistant type 2 diabetes; and (xiii) interstitial lung diseases like idiopathic pulmonary fibrosis, asbestosis, Bleomycin—or Busulfan—induced lung fibrosis.

Therefore, the invention further relates to a method for treating, preventing or ameliorating diseases different to malignant neoplasia comprising arthropathies and osteopathological conditions, autoimmune diseases including transplant rejection, acute and chronic inflammatory diseases, hyperproliferative diseases or neuropathological disorders in a patient comprising administering to said patient a therapeutically effective and tolerable amount of a compound according to the present invention.

The present invention further includes a method for the treatment of mammals, including humans, which are suffering from one of the abovementioned conditions, illnesses, disorders or diseases. The method is characterized in that a pharmacologically active and therapeutically effective and tolerable amount of one or more of the compounds according to this invention, which function by inhibiting histone deacetylases, in particular selectively inhibiting HDAC6, and, by modulating protein acetylation, induces various cellular effects, in particular arresting cell proliferation and/or migration and/or inducing apoptosis, is administered to the subject in need of such treatment.

The invention further includes a method for treating diseases and/or disorders responsive or sensitive to the inhibition of histone deacetylases, in particular sensitive to the inhibition of HDAC6, particularly those diseases mentioned above, such as e.g. cellular neoplasia or diseases different to cellular neoplasia as indicated above, in mammals, including humans, suffering therefrom comprising administering to said mammals in need thereof a pharmacologically active and therapeutically effective and tolerable amount of one or more of the compounds according to the present invention.

The present invention further includes a therapeutic method useful to modulate protein acetylation, gene expression, cell proliferation, cell migration and/or apoptosis in vivo in diseases mentioned above, in particular cancer, comprising administering to a subject in need of such therapy a pharmacologically active and therapeutically effective and tolerable amount of one or more of the compounds according to this invention, which function by inhibiting histone deacetylases, in particular selective for HDAC6.

The invention further relates to the use of the compounds according to the present invention for the production of pharmaceutical compositions which are employed for the treatment and/or prophylaxis and/or amelioration of the diseases, disorders, illnesses and/or conditions as mentioned herein.

The invention further relates to the use of the compounds according to the present invention for the production of pharmaceutical compositions which are employed for the treatment and/or prophylaxis of diseases and/or disorders responsive or sensitive to the inhibition of histone deacetylases, in particular sensitive to inhibition of HDAC6, particularly those diseases mentioned above, such as e.g. cellular neoplasia or diseases different to cellular neoplasia as indicated above.

The invention further relates to the use of the compounds according to the present invention for the production of pharmaceutical compositions having histone deacetylase inhibitory, in particular HDAC6 selective inhibitory activity.

The invention further relates to the use of the compounds according to the present invention for the production of pharmaceutical compositions for inhibiting or treating cellular neoplasia, such as benign or malignant neoplasia, e.g. cancer.

The invention further relates to the use of the compounds according to the present invention for the production of pharmaceutical compositions for the treatment of a disease different to a cellular neoplasia and sensitive to histone deacetylase inhibitor therapy, in particular therapy based on HDAC6 selective inhibitors, such as the non-malignant diseases mentioned before.

The invention further relates to the use of the compounds according to the present invention for the production of pharmaceutical compositions for inhibiting histone deacetylase activity, in particular inhibiting HDAC6 enzymatic activity, in the treatment of diseases responsive to said inhibition or to the functional consequences thereof.

The invention further relates to a method for treating, preventing or ameliorating the diseases, disorders, illnesses and/or conditions mentioned herein in a mammal, in particular a human patient, comprising administering a pharmacologically active and therapeutically effective and tolerable amount of one or more compounds according to the present invention to said mammal in need thereof.

The invention further relates to the compounds according to this invention for use in the treatment and/or prophylaxis of diseases, especially the diseases mentioned.

The invention further relates to pharmaceutical compositions comprising one or more of the compounds according to this invention and a pharmaceutically acceptable carrier or diluent.

The invention further relates to pharmaceutical compositions according to this invention having histone deacetylase inhibitory activity, in particular having HDAC6 inhibitory activity.

The invention further relates to pharmaceutical compositions according to this invention having apoptosis inducing activity and/or anti-migratory activity.

The invention further relates to pharmaceutical compositions according to this invention having chemosensitizing activity.

The invention further relates to the use of a pharmaceutical composition comprising one or more of the compounds according to this invention and a pharmaceutically acceptable carrier or diluent in the manufacture of a pharmaceutical product, such as e.g. a commercial package, for use in the treatment and/or prophylaxis of the diseases as mentioned.

Additionally, the invention relates to an article of manufacture, which comprises packaging material and a pharmaceutical agent contained within said packaging material, wherein the pharmaceutical agent is therapeutically effective for inhibiting the effects of histone deacetylases, in particular the effects of HDAC6, ameliorating the symptoms of an histone deacetylase mediated disorder, and wherein the packaging material comprises a label or package insert which indicates that the pharmaceutical agent is useful for preventing or treating histone deacetylase mediated disorders, and wherein said pharmaceutical agent comprises one or more compounds of formula I according to the invention. The packaging material, label and package insert otherwise parallel or resemble what is generally regarded as standard packaging material, labels and package inserts for pharmaceuticals having related utilities.

The pharmaceutical compositions according to this invention are prepared by processes which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of dermatoses, compounds according to this invention are in particular administered in the form of those pharmaceutical compositions which are suitable for topical application. For the production of the pharmaceutical compositions, the compounds of the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for histone deacetylases inhibitors. Topical application forms (such as ointments) for the treatment of dermatoses thus contain the active compounds in a concentration of, for example, 0.1-99%. The customary dose in the case of systemic therapy (p.o.) is between 0.3 and 30 mg/kg per day, (i. v.) is between 0.3 and 30 mg/kg/h.

The choice of the optimal dosage regime and duration of medication, particularly the optimal dose and manner of administration of the active compounds necessary in each case can be determined by a person skilled in the art on the basis of his/her expert knowledge.

Depending upon the particular disease, to be treated or prevented, additional therapeutic active agents, which are normally administered to treat or prevent that disease, may optionally be coadministered with the compounds according to the present invention. As used herein, additional therapeutic agents that are normally administered to treat or prevent a particular disease are known as appropriate for the disease being treated.

For example, compounds according to this invention may be combined with one or more standard therapeutic agents used for treatment of the diseases as mentioned before.

In one particular embodiment compounds according to this invention may be combined with one or more art-known anti-cancer agents, such as e.g. art-known chemotherapeutic and/or target specific anti-cancer agents as described below.

Examples of known chemotherapeutic anti-cancer agents frequently used in combination therapy include, but are not limited to (i) alkylating/carbamylating agents such as Cyclophosphamid (Endoxan®), Ifosfamid (Holoxan®), Thiotepa (Thiotehpa Lederle®), Melphalan (Alkeran®), or chloroethylnitrosourea (BCNU); (ii) platinum derivatives like cis-Platin (Platinex® BMS), Oxaliplatin or Carboplatin (Cabroplat® BMS); (iii) antimitotic agents/tubulin inhibitors such as vinca alkaloids (vincristine, vinblastine, vinorelbine), taxanes such as Taxol (Paclitaxel®), Taxotere (Docetaxel®) and analogs as well as new formulations and conjugates thereof; epothilones such as Epothilone B (Patupilone®), Azaepothilone (Ixabepilone®) or ZK-EPO, a fully synthetic epothilone B analog, (iv) topoisomerase inhibitors such as anthracyclines (exemplified by Doxorubicin/Adriblastin®), epipodophyllotoxines (examplified by Etoposide/Etopophos®) and Camptothecin analogs (exemplified by Topotecan/Hycamtin®); (v) pyrimidine antagonists such as 5-fluorouracil (5-FU), Capecitabine (Xeloda®), Arabinosylcytosine/Cytarabin (Alexan®) or Gemcitabine (Gemzar®); (vi) purin antagonists such as 6-Mercaptopurine (Puri-Nethol®), 6-Thioguanine or Fludarabine (Fludara®) and finally (vii) folic acid antagonists such as Methotrexate (Farmitrexat®) and Pemetrexed (Alimta®).

Examples of target specific anti-cancer drug classes used in experimental or standard cancer therapy include but are not limited to (i) kinase inhibitors such as e.g. Glivec (Imatinib®), ZD-1839/Iressa (Gefitinib®), Bay43-9006 (Sorafenib®), SU11248 (Sutent®) or OSI-774/Tarceva (Erlotinib®); (ii) proteasome inhibitors such as PS-341 (Velcade®); (iii) heat shock protein 90 inhibitors like 17-AAG; (iv) vascular targeting agents (VTAs) and anti-angiogenic drugs like the VEGF antibody Avastin (Bevacizumab®) or the KDR tyrosine kinase inhibitor PTK787/ZK222584 (Vatalanib®); (v) monoclonal antibodies such as Herceptin (Trastuzumab®), MabThera/Rituxan (Rituximab®) or C225/Erbitux (Cetuximab®) as well as mutants and conjugates of monoclonal antibodies and antibody fragments; (vi) Toll-like receptor agonists as well as oligonucleotide based therapeutics like G-3139/Genasense (Oblimersen®); (vii) protease inhibitors (viii) hormonal therapeutics such as anti-estrogens (e.g. Tamoxifen), anti-androgens (e.g. Flutamide or Casodex), LHRH analogs (e.g. Leuprolide, Goserelin or Triptorelin) and aromatase inhibitors.

Other known targeted anti-cancer agents which can be used for combination therapy include bleomycin, retinoids such as all-trans retinoic acid (ATRA), DNA methyltransferase inhibitors such as the 2-deoxycytidine derivative Decitabine (Docagen®), alanosine, cytokines such as interleukin-2, interferons such as interferon α2 or interferon-γ, TRAIL, DR4/5 agonistic antibodies, FasL- and TNF-R agonists, and finally histone deacetylase inhibitors different to the compounds according to this invention such as SAHA, PXD101, MS275, MGCD0103, Depsipeptide/FK228, NVP-LBH589, Valproic acid (VPA) and butyrates.

As exemplary anti-cancer agents for use in combination with the compounds according to this invention in the cotherapies mentioned herein the following drugs may be mentioned, without being restricted thereto, 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BICALUTAMIDE, BLEOMYCIN, BROXURIDINE, BUSULFAN, CAPECITABINE, CARBOPLATIN, CARBOQUONE, CARMUSTINE, CETRORELIX, CHLORAMBUCIL, CHLORMETHINE, CISPLATIN, CLADRIBINE, CLOMIFENE, CYCLOPHOSPHAMIDE, DACARBAZINE, DACLIZUMAB, DACTINOMYCIN, DAUNORUBICIN, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, LANREOTIDE, LETROZOLE, LEUPRORELIN, LOBAPLATIN, LOMUSTINE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PEGASPARGASE, PEGFILGRASTIM, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLIMUS, SOBUZOXANE, SPIROMUSTINE, STREPTOZOCIN, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRASTUZUMAB, TREOSULFAN, TRIAZIQUONE, TRIMETREXATE, TRIPTORELIN, TROFOSFAMIDE, UREDEPA, VALRUBICIN, VERTEPORFIN, VINBLASTINE, VINCRISTINE, VINDESINE, VINORELBINE and VOROZOLE.

The person skilled in the art is aware on the base of his/her expert knowledge of the total daily dosage(s) and administration form(s) of the additional therapeutic agent(s) coadministered. Said total daily dosage(s) can vary within a wide range.

In practicing the present invention and depending on the details, characteristics or purposes of their uses mentioned above, the compounds according to the present invention may be administered in combination therapy separately, sequentially, simultaneously or chronologically staggered (e.g. as combined unit dosage forms, as separate unit dosage forms, as adjacent discrete unit dosage forms, as fixed or non-fixed combinations, as kit-of-parts or as admixtures) with one or more standard therapeutics, in particular art-known chemotherapeutic or target specific anti-cancer agents, such as those mentioned above.

In this context, the present invention further relates to a combination comprising a first active ingredient, which is at least one compound according to this invention, and a second active ingredient, which is at least one art-known standard therapeutic, for example an art-known anti-cancer agent, such as e.g. one or more of those mentioned herein above, for separate, sequential, simultaneous or chronologically staggered use in therapy, such as e.g. in therapy of those diseases mentioned herein.

The term "combination" according to this invention may be present as a fixed combination, a non-fixed combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously or chronologically staggered.

The present invention further relates to a pharmaceutical composition comprising a first active ingredient, which is at least one compound according to this invention, and a second active ingredient, which is at least one art-known anti-cancer agent, such as e.g. one or more of those mentioned herein above, and, optionally, a pharmaceutically acceptable carrier or diluent, for separate, sequential, simultaneous or chronologically staggered use in therapy.

The present invention further relates to a combination product comprising a.) at least one compound according to this invention formulated with a pharmaceutically acceptable carrier or diluent, and b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a compound according to this invention, and a pharmaceutically acceptable carrier or diluent; a preparation of a second active ingredient, which is an art-known anti-cancer agent, such as one of those mentioned above, and a pharmaceutically acceptable carrier or diluent; for simultaneous, sequential, separate or chronologically staggered use in therapy. Optionally, said kit comprises instructions for its use in therapy, e.g. to treat diseases responsive or sensitive to the inhibition of histone deacetylases, in particular diseases sensitive towards selective inhibition of HDAC6, such as e.g. cellular neoplasia or diseases different to cellular neoplasia as indicated above.

The present invention further relates to a combined preparation comprising at least one compound according to this invention and at least one art-known anti-cancer agent for simultaneous, sequential or separate administration.

In this connection, the present invention further relates to combinations, compositions, formulations, preparations or kits according to the present invention having histone deacetylases inhibitory activity, in particular HDAC6 selective inhibitory activity.

In addition, the present invention further relates to a method for treating in combination therapy diseases responsive or sensitive to the inhibition of histone deacetylases, in particular sensitive to the inhibition of HDAC6, such as e.g. those mentioned above, in a patient comprising administering a combination, composition, formulation, preparation or kit as described herein to said patient in need thereof.

In addition, the present invention further relates to a method for treating diseases responsive or sensitive to the inhibition of histone deacetylases, in particular diseases sensitive towards inhibition of HDAC6, such as e.g. cancer, in a patient comprising administering in combination therapy separately, simultaneously, sequentially or chronologically staggered a pharmaceutically active and therapeutically effective and tolerable amount of a pharmaceutical composition, which comprises a compound according to this invention and a pharmaceutically acceptable carrier or diluent, and a pharmaceutically active and therapeutically effective and tolerable amount of one or more art-known anti-cancer agents, such as e.g. one or more of those mentioned herein, to said patient in need thereof.

In addition, the present invention further relates to the use of a composition, combination, formulation, preparation or kit according to this invention in the manufacture of a pharmaceutical product, such as e.g. a commercial package or a medicament, for treating, preventing, or ameliorating diseases responsive or sensitive to the inhibition of histone deacetylases, in particular sensitive to the selective inhibition of HDAC6, particularly those diseases mentioned herein, such as e.g. benign or malignant neoplasia, particularly cancer.

The present invention further relates to a commercial package comprising one or more compounds of the present invention together with instructions for simultaneous, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, sequential or separate use with one or more compounds according to the present invention.

The compositions, combinations, preparations, formulations, kits or packages mentioned in the context of the combination therapy according to this invention may also include more than one of the compounds according to this invention and/or more than one of the art-known anti-cancer agents mentioned.

The first and second active ingredient of a combination or kit-of-parts according to this invention may be provided as separate formulations (i.e. independently of one another), which are subsequently brought together for simultaneous, sequential, separate or chronologically staggered use in combination therapy; or packaged and presented together as separate components of a combination pack for simultaneous, sequential, separate or chronologically staggered use in combination therapy.

The type of pharmaceutical formulation of the first and second active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a disease responsive or sensitive the inhibition of histone deacetylases, in particular responsive or sensitive to the selective inhibition of HDAC6, particularly one of those diseases mentioned herein.

In addition, compounds according to the present invention can be used in the pre- or post-surgical treatment of cancer.

In further addition, compounds according to the present invention can be used in combination with radiation therapy, in particular in sensitization of cancer patients towards standard radiation therapy.

A combination according to this invention can refer to a composition comprising both the compound(s) according to this invention and the other active anti-cancer agent(s) in a fixed combination (fixed unit dosage form), or a medicament pack comprising the two or more active ingredients as discrete separate dosage forms (non-fixed combination). In case of a medicament pack comprising the two or more active ingredients, the active ingredients are preferably packed into blister cards which are suited for improving compliance.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

1. Biological Investigations

Isolation of HDAC Activity from HeLa Cell Nuclei

HDAC activity is isolated from nuclear HeLa extracts according to a method original described by Dignam et al. (Nucl. Acids Res. 11, pp 1475, 1983). Briefly, nuclei isolated from HeLa cells (CIL SA, Seneffe, Belgium) are resuspended in buffer C (20 mM Hepes pH 7.9, 25% v:v glycerol, 0.42M NaCl, 1.5 mM $MgCl_2$, 0.2 mM EDTA, 0.5 mM PefaBloc and 0.5 mM DTT) and stirred for 30 min on ice. After centrifugation, the supernatant is dialysed against buffer D (40 mM Tris HCl pH 7.4, 100 mM KCl, 0.2 mM EDTA, 0.5 mM DTT and 25% v:v glycerol) for 5 h at 4° C. After dialysis and centrifugation, the supernatant is stored in aliquots at −80° C. and used for Western blot analysis as well as the enzymatic assay as described in the following.

Isolation of rHDAC1, rHDAC3, rHDAC6 and rHDAC8

Human HDAC1 and HDAC6 fused with the FLAG epitope are stably expressed in HEK293 cells while human HDAC3 and HDAC8 fused with the FLAG epitope are overexpressed in baculo-virus infected insect (Sf21) cells. To ensure stability of FLAG-HDAC3 the SMRT protein is co-expressed in the corresponding insect cells. After mass cultivation in DMEM with supplements and 2% fetal calf serum, HEK293 cells are lysed and FLAG-HDAC1 or FLAG-HDAC6 proteins are purified by M2-agarose affinity chromatography as described (Sigma Art. No. A-2220). FLAG-HDAC3 and FLAG-HDAC8 are also purified by M2-agarose affinity chromatography after mass cultivation of the insect cells and cell lysis.

Fractions from the purifications are analysed by Western blotting as well as for enzymatic activity as described below.

Fluorimetric HDAC Activity Assay:

The HDAC enzyme activity assay is done as described by Wegener et al. (Chem. & Biol. 10, 61-68, 2003). Briefly 40 µl of a 1:100 dilution (=0.4 µl) nuclear HeLa extract (mixture of class I and II HDACs), 29 µl enzyme buffer (15 mM Tris HCl pH 8.1, 0.25 mM EDTA, 250 mM NaCl, 10% v:v glycerol) and 1 µl test compound are added to a well of a 96 well microtiter plate and reaction started by addition of 3 µl substrate (Ac-NH-GGK(Ac)-AMC; final concentration 25 µM and final volume 100 µl). After incubation for 90 min at 30° C., reaction is terminated by the addition of 25 µl stop solution (50 mM Tris HCl pH 8, 100 mM NaCl, 0.5 mg/ml trypsine and 2 µM TSA). After incubation at room temperature for further 40 min, fluorescence is measured using a Wallac Victor 1420 multilabel counter (Ex 355 nm, Em 460 nm) for quantification of AMC (7-amino-4-methylcoumarin) generated by trypsine cleavage of the deacetylated peptide. For the calculation of $IC_{50}$ values, the fluorescence in wells without test compound (1% DMSO, negative control) is set as 100% enzymatic activity and the fluorescence in wells with 2 µM TSA (positive control) are set at 0% enzymatic activity. The corresponding $pIC_{50}$ values of the compounds for HDAC inhibitory activity are determined from the concentration-effect curves by means of non-linear regression (Graphpad Prism software).

The HDAC1, HDAC3 and HDAC6 enzymatic assays are done with slight modifications with recombinant FLAG-HDAC1 and FLAG-HDAC6 proteins isolated from HEK293 cell lysates or recombinant FLAG-HDAC3 isolated from insect cells, respectively. The HDAC8 enzymatic assay using recombinant FLAG-HDAC8 isolated from insect cells is done with a different substrate. About 4.5 ng/well FLAG-HDAC1 and 3.1 ng/well FLAG-HDAC6 (dependent on batches and specific activity) are incubated with 6 µM or 10 µM Ac-NH-GGK(Ac)-AMC substrate, respectively, for 3 h at 30° C. About 1.7 ng/well FLAG-HDAC3 is incubated with 6 µM Ac-NH-GGK(Ac)-AMC substrate for 2 h at 30° C., while approximately 130 ng/well FLAG-HDAC8 is incubated with 50 µM Ac-RHK(Ac)K(Ac)-AMC substrate for 3 h at 30° C. Termination of the reaction and all further steps are done as described for HeLa cell nuclear extracts as a source for HDAC enzymatic activity. The corresponding $pIC_{50}$ values of the compounds for HDAC1, HDAC3, HDAC6 and HDAC8 inhibitory activity are determined from the concentration-effect curves by means of non-linear regression.

HDAC activity derived from HeLa cell nuclear extracts is inhibited for examples 1-24 in the range of $pIC_{50}$=4.22 (Ex.

11) to 6.10 (Ex. 15). Recombinant HDAC1 is inhibited in the range of $pIC_{50}$=4.72 (Ex. 11) to 6.52 (Ex. 15), recombinant HDAC3 is inhibited in the range of $pIC_{50}$=4.07 (Ex. 11) to 5.29 (Ex. 22), recombinant HDAC6 is inhibited in the range of $pIC_{50}$=6.26 (Ex. 11) to 8.57 (Ex. 15) and recombinant HDAC8 is inhibited in the range of $pIC_{50}$=5.03 (Ex. 12) to 7.26 (Ex. 23).

In sum the data indicate for all tested compounds that they exhibit the highest activity for the inhibition of HDAC 6. The results are summarized in tables 1a)-e).

TABLE 1a $pIC_{50}$ values of example compounds 1-24 for nuclear HeLa extract inhibitory activity

| Example | HeLa nuclear extract [pIC50] |
|---|---|
| 2, 3, 6-14, 16, 17, 20, 21, 23 | 4.0-5.0 |
| 1, 4, 5, 15, 18, 19, 22, 24 | >5.0-7.0 |

TABLE 1b $pIC_{50}$ values of example compounds 1-24 for rHDAC1 inhibitory activity

| Example | rHDAC1 [pIC50] |
|---|---|
| 2, 6-8, 10-14 | 4.0-5.0 |
| 1, 3-5, 9, 15-24 | >5.0-7.0 |

TABLE 1c $pIC_{50}$ values of example compounds 1-24 for rHDAC3 inhibitory activity

| Example | rHDAC3 [pIC50] |
|---|---|
| 2-14, 16, 17, 19-21, 23 | 4.0-5.0 |
| 1, 15, 18, 22, 24 | >5.0-6.0 |

TABLE 1d $pIC_{50}$ values of example compounds 1-24 for rHDAC6 inhibitory activity

| Example | rHDAC6 [pIC50] |
|---|---|
| 6, 8-13, 20 | 6.0-7.0 |
| 1-5, 7, 14-19, 21-24 | >7.0-9.0 |

TABLE 1e $pIC_{50}$ values of example compounds 1-24 for rHDAC8 inhibitory activity

| Example | rHDAC8 [pIC50] |
|---|---|
| 1-16 | 5.0-6.0 |
| 17-24 | >6.0-8.0 |

Cellular Cytotoxicity Assay:

The anti-proliferative activity of the compounds as described herein, is evaluated with various solid and hematological cancer cell lines using the Alamar Blue (Resazurin) cell viability assay (O'Brien et al, Eur J Biochem 267, 5421-5426, 2000). Resazurin is reduced to the fluorescent resorufin by cellular dehydrogenase activity, correlating with viable, proliferating cells. Test compounds are dissolved as 20 mM solutions in dimethylsulfoxide (DMSO) and subsequently diluted in semi-logarithmic steps. The cancer cell lines are seeded into 96 well flat bottom plates at respective cell densities in a volume of 200 µl per well to allow continuous proliferation during the experiment. 24 hours after seeding 1 µl each of the compound dilutions is added into each well of the 96 well plate. Wells containing untreated control cells are filled with 200 µl DMEM medium containing 0.5% v:v DMSO. The cells are then incubated with the substances for 72 hours at 37° C. in a humidified atmosphere containing 5% carbon dioxide. To determine the viability of the cells, 20 µl of a Resazurin solution (Sigma; 90 mg/l) are added. After 4 hours incubation at 37° C. the fluorescence is measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values. The corresponding $pIC_{50}$ values of the compounds for cytotoxic activity are determined from the concentration-effect curves by means of non-linear regression. The results are summarized in tables 2a)-c).

TABLE 2a $pIC_{50}$ values of example compounds 1-24 for A549 cytotoxic activity

| Example | A549 Cytotoxicity [pIC50] |
|---|---|
| 2-8, 10-14, 16, 17, 19-21 | <4.0 |
| 1, 9, 15, 18, 22-24 | 4.0-6.0 |

TABLE 2b $pIC_{50}$ values of example compounds 1-24 for HeLa cytotoxic activity

| Example | HeLa Cytotoxicity [pIC50] |
|---|---|
| 4-8, 10-13, 16, 20 | <4.0 |
| 1-3, 9, 14, 15, 17-19, 21-24 | 4.0-6.0 |

TABLE 2c $pIC_{50}$ values of example compounds 1, 3-6, 8, 9, 13, 20 and 24 for RKOp21 cytotoxic activity

| Example | RKOp21 Cytotoxicity [pIC50] |
|---|---|
| 3-6, 8, 9, 13, 20 | <4.0 |
| 1, 24 | 4.0-6.0 |

The data indicate that even for a difference of two orders of magnitude for the HDAC inhibitory activity between particular example compounds this is not associated with an increase in cytotoxicity in the same range.

The invention claimed is:
1. A compound of formula I

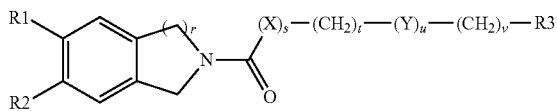 (I)

wherein
R1 is

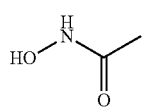

R2 is H;
R3 is hydrogen, —OR4, —NR5R6, or an optionally substituted alicyclic, heteroalicyclic, aromatic or heteroaromatic radical, wherein
the alicyclic radical is a 3- to 6-membered monocyclic group,
the heteroalicyclic radical is a 5- to 6-membered monocyclic group containing one or two heteroatoms, each of which is selected from the group consisting of nitrogen, oxygen and sulfur,
the aromatic radical is phenyl or naphthyl,
the heteroaromatic radical is a 5- to 6-membered monocyclic group or a 9- to 10-membered bicyclic group containing one or two heteroatoms, each of which is selected from the group consisting of nitrogen, oxygen and sulfur,
and
the substituents of the optionally substituted alicyclic, heteroalicyclic, aromatic or heteroaromatic radical are each selected from the group consisting of halogen, 1-4C alkyl, 1-4C alkoxy and phenyl;
R4 is hydrogen, 1-4C alkyl or a substituted or unsubstituted alicyclic, heteroalicyclic, aromatic or heteroaromatic group, wherein each of these groups is as defined as in R3;
R5 and R6 are each independently H or 1-4C alkyl;
X is a single bond, —CH=CH—, —C≡C—, —NH—, oxygen or sulfur;
Y is —NH—, oxygen or sulfur;
r is 1 or 2,
one of s and u is 0 and the other is 1,
t is 0, 1, 2, 3, 4 or 5, and
v is 0, 1, 2, 3 or 4;
or a salt thereof.
2. A compound of formula I according to claim 1, wherein
t is 0 or 1, and
v is 0, 1 or 2,
or a salt thereof.
3. A compound of formula I according to claim 1, wherein
s is 1,
t is 1,
u is 0, and
v is 0, 1 or 2,
or a salt thereof.
4. A compound of formula I according to claim 1, wherein
s is 0,
t is 1,
u is 1, and
v is 0, 1 or 2,
or a salt thereof.
5. A compound of formula I according to claim 1, wherein
R3 is hydrogen, —OR4, —NR5R6, or an optionally substituted alicyclic, heteroalicyclic, aromatic or heteroaromatic radical, wherein
the alicyclic radical is selected from the group consisting of cyclopropyl and cyclobutyl,
the heteroalicyclic radical is tetrahydrofuryl,
the aromatic radical is phenyl,
the heteroaromatic radical is selected from the group consisting of imidazolyl, pyridyl, indolyl and quinolinyl, and
the substituents of the optionally substituted alicyclic, heteroalicyclic, aromatic or heteroaromatic radical are each selected from the group consisting of —CH$_3$, —OCH$_3$ and phenyl;
R4 is —CH$_3$ or phenyl;
R5 and R6 are each independently H or —CH$_3$;
Y is oxygen;
s is 0, and
u is 1,
or a salt thereof.
6. A compound of formula I according to claim 1, wherein
R3 is hydrogen, —OR4, —NR5R6, or an optionally substituted alicyclic, heteroalicyclic, aromatic or heteroaromatic radical, wherein
the alicyclic radical is selected from the group consisting of cyclopropyl and cyclobutyl,
the heteroalicyclic radical is tetrahydrofuryl,
the aromatic radical is phenyl,
the heteroaromatic radical is selected from the group consisting of imidazolyl, pyridyl, indolyl and quinolinyl, and
the substituents of the optionally substituted alicyclic, heteroalicyclic, aromatic or heteroaromatic radical are each selected from the group consisting of —CH$_3$, —OCH$_3$ and phenyl;
R4 is —CH$_3$ or phenyl;
R5 and R6 are each independently H or —CH$_3$;
X is a single bond, —C≡C—, —NH—, or oxygen;
s is 1, and
u is 0,
or a salt thereof.
7. A compound of formula I according to claim 1, wherein
r is 1,
or a salt thereof.
8. A compound of formula I according to claim 1, wherein
R1 is

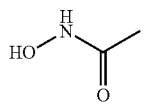

R2 is H, and
r is 2,
or a salt thereof.
9. A compound, which is
9.1. N-Hydroxy-2-(indol-3-ylacetyl)-1,2,3,4-tetrahydroisoquinoline-6-carboxamide,
9.2. N-Hydroxy-2-(pyridin-2-ylacetyl)-1,2,3,4-tetrahydroisoquinoline-6-carboxamide, 9.3. 2-(Cyclobutylcarbonyl)-N-hydroxy-1,2,3,4-tetrahydroisoquinoline-6-carboxamide,
9.4. N6-Hydroxy-N2-methyl-3,4-dihydroisoquinoline-2,6(1H)-dicarboxamide,
9.5. N6-Hydroxy-N2-(3-methoxypropyl)-3,4-dihydroisoquinoline-2,6(1H)-dicarboxamide,
9.6. 3-Methoxypropyl-6-(hydroxycarbamoyl)-3,4-dihydroisoquinoline-2(1H)-carboxylate,
9.7. N-Hydroxy-2-(3-pyridin-3-ylpropanoyl)-1,2,3,4-tetrahydroisoquinoline-6-carboxamide,
9.8. N-Hydroxy-2-(pyridin-3-ylacetyl)-1,2,3,4-tetrahydroisoquinoline-6-carboxamide,
9.9. 2-[4-(Dimethylamino)butanoyl]-N-hydroxy-1,2,3,4-tetrahydroisoquinoline-6-carboxamide,
9.10. N-Hydroxy-2-[(2-methyl-1H-imidazol-1-yl)acetyl]-1,2,3,4-tetrahydroisoquinoline-6-carboxamide,
9.11. N-Hydroxy-2-[(2-methoxyethoxy)acetyl]-1,2,3,4-tetrahydroisoquinoline-6-carboxamide,
9.12. 2-Acetyl-N-hydroxy-1,2,3,4-tetrahydroisoquinoline-6-carboxamide,
9.13. N-Hydroxy-2-(tetrahydrofuran-3-ylcarbonyl)-1,2,3,4-tetrahydroisoquinoline-6-carboxamide,
9.14. N-Hydroxy-2-(pyridin-2-ylacetyl)-1,2,3,4-tetrahydroisoquinoline-6-carboxamide,
9.15. N-Hydroxy-2-[(5-methoxy-1H-indol-2-yl)carbonyl]-1,2,3,4-tetrahydroisoquinoline-6-carboxamide,
9.16. N-Hydroxy-2-(cyclopropylcarbonyl)-1,2,3,4-tetrahydroisoquinoline-6-carboxamide,
9.17. 2-But-2-ynoyl-N-hydroxy-1,2,3,4-tetrahydroisoquinoline-7-carboxamide,
9.18. N-Hydroxy-2-(1H-indol-3-ylacetyl)-1,2,3,4-tetrahydroisoquinoline-7-carboxamide,
9.19. N-Hydroxy-2-(pyridin-3-ylacetyl)-1,2,3,4-tetrahydroisoquinoline-7-carboxamide,
9.20. N-Hydroxy-2-(tetrahydrofuran-3-ylcarbonyl)-1,2,3,4-tetrahydroisoquinoline-7-carboxamide,
9.21. N-Hydroxy-2-(pyridin-2-ylacetyl)-1,2,3,4-tetrahydroisoquinoline-7-carboxamide,
9.22. N7-Hydroxy-N2-(2-phenylethyl)-3,4-dihydroisoquinoline-2,7(1H)-dicarboxamide,
9.23. N-Hydroxy-2-(4-methylbenzoyl)-1,2,3,4-tetrahydroisoquinoline-7-carboxamide,
9.24. N-Hydroxy-2-[(5-methoxy-1H-indol-2-yl)carbonyl]-1,2,3,4-tetrahydroisoquinoline-7-carboxamide,
9.25. 2-Acetyl-N-hydroxy-1,2,3,4-tetrahydroisoquinoline-7-carboxamide,
9.26. Pyridin-3-ylmethyl 5-(hydroxycarbamoyl)-1,3-dihydro-2H-isoindole-2-carboxylate,
9.27. N-Hydroxy-2-(quinolin-2-ylcarbonyl)isoindoline-5-carboxamide,
9.28. N-Hydroxy-2-(quinolin-6-ylcarbonyl)isoindoline-5-carboxamide,
9.29. N-Hydroxy-2-(isoquinolin-3-ylcarbonyl)isoindoline-5-carboxamide,
9.30. 2-(Biphenyl-4-ylcarbonyl)-N-hydroxyisoindoline-5-carboxamide,
9.31. N-Hydroxy-2-(3-pyridin-3-ylpropanoyl)-1,2,3,4-tetrahydroisoquinoline-7-carboxamide,
9.32. N7-Hydroxy-N2-(3-methoxypropyl)-3,4-dihydroisoquinoline-2,7(1H)-dicarboxamide,
9.34. 3-Methoxypropyl 7-(hydroxycarbamoyl)-3,4-dihydroisoquinoline-2(1H)-carboxylate,
9.35. N7-Hydroxy-N2-methyl-3,4-dihydroisoquinoline-2,7(1H)-dicarboxamide,
9.36. 2-(Cyclobutylcarbonyl)-N-hydroxy-1,2,3,4-tetrahydroisoquinoline-7-carboxamide,
9.37. N-Hydroxy-2-(1H-indol-5-ylcarbonyl)-1,2,3,4-tetrahydroisoquinoline-7-carboxamide,
9.38. N-Hydroxy-2-[(2-methoxyethoxy)acetyl]-1,2,3,4-tetrahydroisoquinoline-7-carboxamide,
9.39. N-Hydroxy-2-[3-(2-methyl-1H-imidazol-1-yl)propanoyl]-1,2,3,4-tetrahydroisoquinoline-7-carboxamide,
9.40. Benzyl 6-(hydroxycarbamoyl)-3,4-dihydroisoquinoline-2(1H)-carboxylate,
9.41. N-Hydroxy-2-(phenoxyacetyl)-1,2,3,4-tetrahydroisoquinoline-6-carboxamide,
9.42. N-Hydroxy-2-(4-methylbenzoyl)-1,2,3,4-tetrahydroisoquinoline-6-carboxamide,
9.43. N6-Hydroxy-N2-[2-(1H-indol-3-yl)ethyl]-3,4-dihydroisoquinoline-2,6(1H)-dicarboxamide,
9.44. N6-Hydroxy-N2-benzyl-3,4-dihydroisoquinoline-2,6(1H)-dicarboxamide,
9.45. N6-Hydroxy-N2-(2-phenoxyethyl)-3,4-dihydroisoquinoline-2,6(1H)-dicarboxamide, or
9.46. N-hydroxy-2-(1H-Indol-5-ylcarbonyl)-1,2,3,4-tetrahydroisoquinoline-6-carboxamide,
or a salt thereof.

10. A compound of formula I according to claim 9, which is
9.1. N-Hydroxy-2-(indol-3-ylacetyl)-1,2,3,4-tetrahydroisoquinoline-6-carboxamide
9.2. N-Hydroxy-2-(pyridin-2-ylacetyl)-1,2,3,4-tetrahydroisoquinoline-6-carboxamide,
9.3. 2-(Cyclobutylcarbonyl)-N-hydroxy-1,2,3,4-tetrahydroisoquinoline-6-carboxamide,
9.4. N6-Hydroxy-N2-methyl-3,4-dihydroisoquinoline-2,6(1H)-dicarboxamide,
9.5. N6-Hydroxy-N2-(3-methoxypropyl)-3,4-dihydroisoquinoline-2,6(1H)-dicarboxamide,
9.6. 3-Methoxypropyl-6-(hydroxycarbamoyl)-3,4-dihydroisoquinoline-2(1H)-carboxylate,
9.7. N-Hydroxy-2-(3-pyridin-3-ylpropanoyl)-1,2,3,4-tetrahydroisoquinoline-6-carboxamide,
9.8. N-Hydroxy-2-(pyridin-3-ylacetyl)-1,2,3,4-tetrahydroisoquinoline-6-carboxamide,
9.10. N-Hydroxy-2-[(2-methyl-1H-imidazol-1-yl)acetyl]-1,2,3,4-tetrahydroisoquinoline-6-carboxamide,
9.11. N-Hydroxy-2-[(2-methoxyethoxy)acetyl]-1,2,3,4-tetrahydroisoquinoline-6-carboxamide,
9.12. 2-Acetyl-N-hydroxy-1,2,3,4-tetrahydroisoquinoline-6-carboxamide,
9.13. N-Hydroxy-2-(tetrahydrofuran-3-ylcarbonyl)-1,2,3,4-tetrahydroisoquinoline-6-carboxamide,
9.14. N-Hydroxy-2-(pyridin-2-ylacetyl)-1,2,3,4-tetrahydroisoquinoline-6-carboxamide,
9.15. N-Hydroxy-2-[(5-methoxy-1H-indol-2-yl)carbonyl]-1,2,3,4-tetrahydroisoquinoline-6-carboxamide,
9.16. N-Hydroxy-2-(cyclopropylcarbonyl)-1,2,3,4-tetrahydroisoquinoline-6-carboxamide,
9.17. 2-But-2-ynoyl-N-hydroxy-1,2,3,4-tetrahydroisoquinoline-7-carboxamide,
9.18. N-Hydroxy-2-(1H-indol-3-ylacetyl)-1,2,3,4-tetrahydroisoquinoline-7-carboxamide,
9.19. N-Hydroxy-2-(pyridin-3-ylacetyl)-1,2,3,4-tetrahydroisoquinoline-7-carboxamide,
9.20. N-Hydroxy-2-(tetrahydrofuran-3-ylcarbonyl)-1,2,3,4-tetrahydroisoquinoline-7-carboxamide,
9.21. N-Hydroxy-2-(pyridin-2-ylacetyl)-1,2,3,4-tetrahydroisoquinoline-7-carboxamide,
9.22. N7-Hydroxy-N2-(2-phenylethyl)-3,4-dihydroisoquinoline-2,7(1H)-dicarboxamide, 9.23. N-Hydroxy-2-(4-methylbenzoyl)-1,2,3,4-tetrahydroisoquinoline-7-carboxamide,
9.24. N-Hydroxy-2-[(5-methoxy-1H-indol-2-yl)carbonyl]-1,2,3,4-tetrahydroisoquinoline-7-carboxamide,
9.25. 2-Acetyl-N-hydroxy-1,2,3,4-tetrahydroisoquinoline-7-carboxamide,
9.26. Pyridin-3-ylmethyl 5-(hydroxycarbamoyl)-1,3-dihydro-2H-isoindole-2-carboxylate,
9.27. N-Hydroxy-2-(quinolin-2-ylcarbonyl)isoindoline-5-carboxamide,
9.28. N-Hydroxy-2-(quinolin-6-ylcarbonyl)isoindoline-5-carboxamide,
9.29. N-Hydroxy-2-(isoquinolin-3-ylcarbonyl)isoindoline-5-carboxamide,
9.30. 2-(Biphenyl-4-ylcarbonyl)-N-hydroxyisoindoline-5-carboxamide,
9.31. N-Hydroxy-2-(3-pyridin-3-ylpropanoyl)-1,2,3,4-tetrahydroisoquinoline-7-carboxamide,
9.32. N7-Hydroxy-N2-(3-methoxypropyl)-3,4-dihydroisoquinoline-2,7(1H)-dicarboxamide,
9.34. 3-Methoxypropyl 7-(hydroxycarbamoyl)-3,4-dihydroisoquinoline-2(1H)-carboxylate,
9.35. N7-Hydroxy-N2-methyl-3,4-dihydroisoquinoline-2,7(1H)-dicarboxamide,
9.36. 2-(Cyclobutylcarbonyl)-N-hydroxy-1,2,3,4-tetrahydroisoquinoline-7-carboxamide,
9.37. N-Hydroxy-2-(1H-indol-5-ylcarbonyl)-1,2,3,4-tetrahydroisoquinoline-7-carboxamide,
9.38. N-Hydroxy-2-[(2-methoxyethoxy)acetyl]-1,2,3,4-tetrahydroisoquinoline-7-carboxamide,
9.39. N-Hydroxy-2-[3-(2-methyl-1H-imidazol-1-yl)propanoyl]-1,2,3,4-tetrahydroisoquinoline-7-carboxamide,
9.40. Benzyl 6-(hydroxycarbamoyl)-3,4-dihydroisoquinoline-2(1H)-carboxylate,
9.41. N-Hydroxy-2-(phenoxyacetyl)-1,2,3,4-tetrahydroisoquinoline-6-carboxamide,
9.42. N-Hydroxy-2-(4-methylbenzoyl)-1,2,3,4-tetrahydroisoquinoline-6-carboxamide,
9.43. N6-Hydroxy-N2-[2-(1H-indol-3-yl)ethyl]-3,4-dihydroisoquinoline-2,6(1H)-dicarboxamide,
9.44. N6-Hydroxy-N2-benzyl-3,4-dihydroisoquinoline-2,6(1H)-dicarboxamide,
9.45. N6-Hydroxy-N2-(2-phenoxyethyl)-3,4-dihydroisoquinoline-2,6(1H)-dicarboxamide, or
9.46. N-hydroxy-2-(1H-Indol-5-ylcarbonyl)-1,2,3,4-tetrahydroisoquinoline-6-carboxamide,
or a salt thereof.

11. A pharmaceutical composition, comprising a compound of formula I as claimed in claim 1 or a pharmaceutically acceptable salt thereof together with one or more pharmaceutical excipients.

12. The pharmaceutical composition according to claim 11, which comprises a further active ingredient.

13. The pharmaceutical composition according to claim 12, wherein the further active ingredient is an anti-cancer drug.

14. A method for treating cervical carcinoma, non-small cell lung tumor or colon adenocarcinoma, comprising administering to said patient a therapeutically effective and tolerable amount of a compound of formula I as claimed in claim 1 or a pharmaceutically acceptable salt thereof.

15. A method for treating cervical carcinoma, non-small cell lung tumor or colon adenocarcinoma, comprising administering to said patient a therapeutically effective and tolerable amount of a compound of formula I as claimed in claim 9 or a pharmaceutically acceptable salt thereof.

16. A method for treating a solid tumor of the breast, bladder, colon, thyroid, head and neck, lung, mesothelioma, ovary, pancreas, prostate, rectum, renal, retinoblastoma, or Wilms tumor, or leukemia, lymphoma, non-Hodgkins disease, myeloid leukemia, Hodgkins disease, multiple myeloma, T-cell lymphoma, or myelodysplastic syndrome, comprising administering to said patient a therapeutically effective and tolerable amount of a compound of formula I as claimed in claim 1 or a pharmaceutically acceptable salt thereof.

17. A method for treating a solid tumor of the breast, bladder, colon, thyroid, head and neck, lung, mesothelioma, ovary, pancreas, prostate, rectum, renal, retinoblastoma, or Wilms tumor, or leukemia, lymphoma, non-Hodgkins disease, myeloid leukemia, Hodgkins disease, multiple myeloma, T-cell lymphoma, or myelodysplastic syndrome, comprising administering to said patient a therapeutically effective and tolerable amount of a compound of formula I as claimed in claim 9 or a pharmaceutically acceptable salt thereof.

* * * * *

UNITED STATES PATENT AND TRADEMARK OFFICE
CERTIFICATE OF CORRECTION

PATENT NO. : 8,575,193 B2  
APPLICATION NO. : 12/921821  
DATED : November 5, 2013  
INVENTOR(S) : Maier et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 135 days.

Signed and Sealed this
Seventeenth Day of February, 2015

Michelle K. Lee
*Deputy Director of the United States Patent and Trademark Office*